US009290782B2

(12) United States Patent
Posewitz et al.

(10) Patent No.: US 9,290,782 B2
(45) Date of Patent: Mar. 22, 2016

(54) MODIFIED ALGAE FOR IMPROVED BIOFUEL PRODUCTIVITY

(75) Inventors: Matthew C. Posewitz, Golden, CO (US); Randor Radakovits, Denver, CO (US); Robert Jinkerson, Golden, CO (US); Victoria H. Work, Golden, CO (US); Jonathan E. Meuser, La Jolla, CA (US)

(73) Assignee: COLORADO SCHOOL OF MINES, Golden, CO (US)

( * ) Notice: Subject to any disclaimer, the term of this patent is extended or adjusted under 35 U.S.C. 154(b) by 0 days.

(21) Appl. No.: 13/430,383

(22) Filed: Mar. 26, 2012

(65) Prior Publication Data
US 2012/0329099 A1 Dec. 27, 2012

Related U.S. Application Data

(60) Provisional application No. 61/467,919, filed on Mar. 25, 2011.

(51) Int. Cl.
C12N 9/24 (2006.01)
C12N 15/82 (2006.01)
C12P 19/04 (2006.01)
C12P 19/14 (2006.01)
C12N 9/44 (2006.01)

(52) U.S. Cl.
CPC ............. C12P 19/04 (2013.01); C12N 9/2451 (2013.01); C12P 19/14 (2013.01); C12Y 302/01068 (2013.01)

(58) Field of Classification Search
CPC .......................... C12N 9/2497; C12N 15/8245
USPC .................................. 435/168, 252.3, 471, 99
See application file for complete search history.

(56) References Cited

PUBLICATIONS

Work et al., Eukaryotic Cell, 9(8), 1251-1261, Aug. 2010.*
Chochois et al. "Hydrogen Production in Chlamydomonas: Photosystem II-dependent and—independent Pathways Differ in their Requirement for Starch Metabolism", Plant Physiol. 151:631-640 (2009).
Datar et al. "Hydrogen Production from the Fermentation of Corn Stover Biomass Pretreated with a Steam-Explosion Process", Int. J. Hyd. Energy 32:932-939 (2007).
Dauvillee et al. "Biochemical Characterization of Wild-type and Mutant Isoamylases of *Chlamydomonas reinhardtii* Supports a Function of the Multimeric Enzyme Organization in Amylopectin Maturation", Plant Physiol. 125:1723-1731 (2001).
Dauvillee et al. "Novel, Starch-like Polysaccharides are Synthesized by an Unbound Form of Granule-bound Starch Synthase in Glycogen-accumulating Mutants of *Chlamydomonas reinhardtii*", Plant Physiol. 119:321-329 (1999).
Dauville et al. "The Debranching Enzyme Complex Missing in Glycogen Accumulating Mutants of *Chlamydomonas reinhardtii* Displays an Isoamylase-type Specificty", Plant Sci. 157:145-156 (2000).
Dauvillee et al. "Two Loci Control Phytoglycogen Production in the Monocellular Green Alga *Chlamydomonas reinhardtii*", Plant Physiol. 125:1710-1722 (2001).
Dismukes et al. "Aquatic Phototrophs: Efficient Alternatives to Land-based Crops for Biofuels", Curr. Opin. Biotechnol. 19:235-240 (2008).
Ghirardi et al. "Hydrogenases and Hydrogen Photoproduction in Oxygenic Photosynthetic Organisms", Annu. Rev. Plant Biol. 58:71-91 (2007).
Gocze et al. "Factors Underlying the Variability of Lipid Droplet Fluorescence in Ma-10 Leydig Tumor-Cells", Cytometry 17:151-158 (1994).
Gorman et al. "Cytochrome f and Plastocyanin: their Sequence in the Photosynthetic Electron Transport Chain of *Chlamydomonas reinhardii*", Proc. Nat. Acad. Sci. U.S.A. 54:1665-1669 (1985).
Grossman et al. "Novel Metabolism in Chlamydomonas through the Lens of Genomics", Curr. Opin. Plant Biol. 10:190-198 (2007).
Hankamer et al. "Photosynthetic Biomass and H2 Production by Green Algae: from Bioengineering to Bioreactor Scale-up", Physiol. Plant 131:10-21 (2007).
Hemschemeier et al. "Analytical Approaches to Photobiological Hydrogen Production in Unicellular Green Algae", Photosynth Res. , 102: 523-540 (2009).
Hu et al. "Microalgal Triacylglycerols as Feedstocks for Biofuel Production: Perspectives and Advances", Plant J. 54:621-639 (2008).
Kolber et al. "Measurements of Variable Chlorophyll Fluorescence using Fast Repetition Rate Techniques: Defining Methodology and Experimental Protocols", Biochem. Biophys. Acta 1367:88-106 (1998).
Li et al. "Chlamydomonas Starchless Mutant Defective in ADP-glucose Pyrophosphorylase Hyper-accumulates Triacylglycerol", Metab. Eng., pp. 1-5 (2010).
Libessart et al. "Storage, Photosynthesis and Growth: The Conditional Nature of Mutations Affecting Starch Synthesis and Structure in Chlamydomonas", Plant Cell 7:1117-1127 (1995).
Lumbreras et al. "Efficient Foreign Gene Expression in *Chlamydomonas reinhardtii* Mediated by an Endogenous Intron", Plant J. 14(4): 441-447 (1998).
Martin et al. "Gametic Differentiation in *Chlamydomonas reinhardtii*. I. Production of Gametes and their Fine Structure", J. Cell Biol. 67:587-605 (1975).
Melis et al. "Sustained Photobiological Hydrogen Gas Production upon Reversible Inactivation of Oxygen Evolution in the Green Alga *Chlamydomonas reinhardtii*", Plant Physiol. 122:127-135 (2000).
Merchant et al. "The Chlamydomonas Genome Reveals the Evolution of Key Animal and Plant Functions", Science 318:245-251 (2007).

(Continued)

*Primary Examiner* — Maryam Monshipouri
(74) *Attorney, Agent, or Firm* — Dorsey & Whitney LLP

(57) ABSTRACT

Methods, processes, and systems for the production of lipids and starch from modified algae are disclosed. In one embodiment, the modified algae over-expresses isoamylase and accumulates much higher amounts of starch than unmodified algae. In some embodiments, the modified algae comprises one or more copies of an isoamylase expression construct. In one embodiment, the modified algae is a sta7 *Chlamydomonas reinhardtii* mutant with a starchless phenotype that has been complemented with one or more copies of the wild-type genomic STA7 isoamylase gene construct. The complemented, modified algae accumulates much greater amount of starch than an unmodified algae and may be used to produce large amounts of starch and/or lipids.

16 Claims, 7 Drawing Sheets

(56) References Cited

PUBLICATIONS

Moellering et al. "RNA Interference Silencing of a Major Lipid Droplet Protein Affects Lipid Droplet Size in *Chlamydomonas reinhardtii*", Eukaryot. Cell, vol. 9 No. 1, pp. 97-106, 2010.

Mouille et al. "Preamylopectin Processing: A Mandatory Step for Starch Biosynthesis in Plants", Plant Cell 8:1353-1366 (1996).

Pendergrass, "Aerobic Bacteria by GC-FAME Method 0801", NIOSH Manual of Analytical Methods, $4^{th}$ ed. (1998).

Posewitz et al. "Hydrogen Photoproduction is Attenuated by Disruption of an Isoamylase Gene in *Chlamydomonas reinhardtii*", Plant Cell 16:2151-2163 (2004).

Posewitz et al. "Identification of Genes Required for Hydrogenase Activity in *Chlamydomonas reinhardtii*", Biochem. Soc. Trans. 33:102-104 (2005).

Ramazanov et al. "Isolation and Characterization of a Starchless Mutant of *Chlorella pyrenoidosa* STL-PI with a High Growth Rate and High Protein and Polyunsaturated Fatty Acid Content", Phycol. Res. 54:255-259 (2006).

Sager et al. "Nutritional Control of Sexuality in *Chlamydomonas reinhardtii*", J. Gen. Physiol., 37:729-742 (1954).

Schenk et al. "Second Generation Biofuels: High-Efficiency Microalgae for Biodiesel Production", Bioenerg. Res. 1:20-43 (2008).

Wang et al. "Algal Lipid Bodies: Stress Induction, Purification and Biochemical Characterization in Wild-type and Starchless *Chlamydomonas reinhardtii*", Eukaryot. Cell 8:1856-1868 (2009).

Wykoff et al. "The Regulation of Photosynthetic Electron Transport During Nutrient Deprivation in *Chlamydomonas reinhardtii*", Plant Physiol. 117:129-139 (1998).

Zabawinski et al. "Starchless Mutants of *Chlamydomonas reinhardtii* Lack the Small Subunit of a Heterotetrameric ADP-Glucose Pyrophosphorylase", J. Bacteriol. 183:1069-1077 (2001).

\* cited by examiner

SEQUENCE LISTING

```
<160> NUMBER OF SEQ ID NOS: 3

<210> SEQ ID NO 1
<211> LENGTH: 875
<212> TYPE: PRT
<213> ORGANISM: Chlamydomonas reinhardtii

<400> SEQUENCE: 1

Met Leu Leu Gln Ala Pro Gly Leu Ala Pro Gly Ser Ala Arg Arg Gln
1               5                   10                  15

Ala Ala Cys Ser Val Ala Arg Glu Ala Thr Asn Val Arg Ile Val Thr
                20                  25                  30

Ala Pro Ala Leu Thr Pro Gly Arg Ala Gly Val Ser Gly Arg Arg Ile
            35                  40                  45

Leu Pro Pro Ser Arg Val Val Ser Val Glu Leu Glu Ala Pro Thr Leu
    50                  55                  60

Ser Ser Ser Pro Ala Thr Val Ser Thr Lys Lys Leu Phe Cys Glu Pro
65                  70                  75                  80

Ser Gly Gln Pro Ala Ser Thr Ala Tyr Gly Pro Ala Leu Thr Gly Arg
                85                  90                  95

Pro Ala Pro Leu Gly Ala Ser Ile Asp Ala Asp Thr Gly Ala Ile Asn
            100                 105                 110

Phe Ser Val Phe Ser Ser Ser Ala Glu Ser Val Ser Leu Val Leu Phe
        115                 120                 125

Thr Glu Ala Asp Leu Asn Ala Gly Arg Ala Thr Phe Glu Ile Pro Leu
    130                 135                 140

Asp Pro Tyr Val Asn Arg Thr Gly Asp Val Trp His Ile Met Leu Pro
145                 150                 155                 160

Asp Leu Arg Asp Asp Leu Leu Tyr Gly Tyr Arg Val Glu Gly Val His
                165                 170                 175

Gln Glu Glu Asp Lys Asp Tyr Pro Gly Met Arg His Asp Lys Arg Arg
            180                 185                 190

Val Val Leu Asp Pro Tyr Ala Val Ala Val Leu Asn Arg Arg Arg Trp
        195                 200                 205

Gly Gln Met Gly Pro Asn Leu Pro Tyr Gly Glu Glu Gly Val Leu Gly
    210                 215                 220

Val Met Pro Thr Trp Pro Gln Ala Ala Ala Leu Pro Ala Ala Arg
225                 230                 235                 240

Gly Ser Ala Phe Asp Trp Glu Gly Asp Thr Pro Leu Asn Leu Pro Met
                245                 250                 255

Glu Ser Leu Val Ile Tyr Glu Ala His Val Arg Gly Phe Thr Ala His
            260                 265                 270

Ala Ser Ser Gly Val Ala Ala Pro Gly Thr Tyr Ala Gly Met Val Glu
        275                 280                 285

Arg Leu Asp Tyr Leu Lys Ser Leu Gly Val Asn Ala Ile Glu Leu Leu
    290                 295                 300
```

```
                                   -continued
Pro Val Phe Glu Phe Asn Glu Leu Glu Tyr Tyr Ser Gln Ile Pro Gly
305                 310                 315                 320

Ser Asp Gln Tyr Arg Phe Asn Phe Trp Gly Tyr Ser Thr Val Asn Tyr
            325                 330                 335

Phe Ser Pro Met Gly Arg Phe Ser Ala Ala Val Gly Gln Gly Ala Pro
                340                 345                 350

Ala Arg Ala Ser Cys Asp Glu Phe Lys Gln Leu Val Lys Glu Cys His
            355                 360                 365

Arg Arg Gly Ile Glu Val Ile Leu Asp Val Val Phe Asn His Thr Ala
        370                 375                 380

Glu Gly Asn Glu Arg Gly Pro Thr Ile Ser Phe Arg Gly Leu Asp Asn
385                 390                 395                 400

Arg Val Tyr Tyr Met Leu Ala Pro Gly Gly Glu Tyr Tyr Asn Tyr Ser
                405                 410                 415

Gly Cys Gly Asn Thr Leu Asn Cys Asn Gln Pro Val Val Arg Gln Phe
            420                 425                 430

Ile Leu Asp Cys Leu Lys His Trp Val Thr Glu Tyr His Val Asp Gly
        435                 440                 445

Phe Arg Phe Asp Leu Ala Ser Ile Leu Thr Arg Ala His Ser Ala Trp
450                 455                 460

His Pro Gln Gln Tyr Asp Gln Glu Thr Gly Gln Arg Val Ala Met Ser
465                 470                 475                 480

Ser Gly Gly Ala Ile Val Thr Ala Glu Gly Ile Met Thr Asp Gly Ala
                485                 490                 495

Gly Val Pro Thr Gly Tyr Pro Leu Ala Asp Pro Pro Leu Val Glu Ser
            500                 505                 510

Ile Ser Glu Asp Pro Val Leu Arg Asn Thr Lys Met Ile Ala Glu Ala
        515                 520                 525

Trp Asp Cys Asp Gly Leu Asn Gln Val Gly Ala Phe Pro His Tyr Gly
530                 535                 540

Gly Arg Trp Ser Glu Trp Asn Gly Lys Phe Arg Asp Val Val Arg Asn
545                 550                 555                 560

Phe Ile Lys Gly Thr Asp Gly Pro Trp Ala Gly Asp Phe Ala Ser Ala
                565                 570                 575

Ile Cys Gly Ser Pro Asn Ile Tyr Ala Asn Asn Thr Pro His Glu Thr
            580                 585                 590

Asp Trp Trp Ala Asn Asn Gly Arg Gln Trp Lys Gly Gly Arg Gly
        595                 600                 605

Pro His Ala Ser Ile Asn Phe Val Ala Ala His Asp Gly Phe Thr Leu
610                 615                 620

Ala Asp Met Val Ala Tyr Asn Asn Lys His Asn Glu Ala Asn Gly Glu
625                 630                 635                 640

Asn Asn Arg Asp Gly Glu Gln His Asn Asn Ser Trp Asn Cys Gly Glu
                645                 650                 655

Glu Gly Pro Thr Thr Lys Trp Glu Val Asn Arg Leu Arg Gln Arg Gln
            660                 665                 670

Met Arg Asn Leu Thr Gly Ala Leu Leu Leu Ser Cys Gly Val Pro Met
        675                 680                 685

Ile Asn Met Gly Asp Glu Tyr Gly His Ser Lys Gly Asn Gly Asn Asn
690                 695                 700

Thr Tyr Cys His Asp Ser Glu Leu Asn Tyr Leu Arg Trp Asp Gln Leu
705                 710                 715                 720

Ala Glu Asp Pro His Gly Phe Asn Arg Phe Val Arg Leu Leu Ile His
```

```
                    725                 730                 735
Phe Arg Arg Ala Thr Pro Ala Leu Gln Arg Thr Thr Phe Val Asn Asp
                740                 745                 750

Lys Asp Ile Gln Trp His Gly Glu Leu Pro Asn Thr Pro Asp Trp Thr
            755                 760                 765

Asp Thr Ser Arg Leu Val Ala Phe Thr Leu His Asp Gly Lys Gly Gly
        770                 775                 780

Gly Leu Tyr Val Ala Phe Asn Thr Ser His Leu Pro Lys Leu Leu Gln
785                 790                 795                 800

Leu Pro Lys Trp Gly Gly Arg Val Trp Gln Pro Leu Val Asp Thr Ser
                805                 810                 815

Lys Val Ala Pro Tyr Asp Phe Leu Ala Val Asp Gly Val Leu Ser Ala
            820                 825                 830

Glu Asp Val Ala Ala Ala Arg Arg Gln Met Ala Met Trp Thr Ala Asp
        835                 840                 845

His Thr Tyr Pro Val Leu Pro Trp Ser Cys Ile Val Leu Gln Ser Ala
    850                 855                 860

Pro Glu Asp Pro Ala Ala Thr Ser Met Ile Lys
865                 870                 875

<210> SEQ ID NO 2
<211> LENGTH: 2628
<212> TYPE: DNA
<213> ORGANISM: Chlamydomonas reinhardtii

<400> SEQUENCE: 2
atgcttctgc aagcccctgg cctcgcgccg ggctcggctc gtcgccaggc agcctgcagc      60
gtggctcgcg aggcaaccaa cgtgcgcatt gtgacagcac ctgctttgac acccgggcgc     120
gctggagttt ctggccggcg tatcctcccg ccctcgcgcg tcgtgtccgt ggagctggag     180
gccccgacgc tgtcgtcgag ccctgcgact gtcagcacca agaagttgtt ctgcgagccg     240
agcgggcagc ccgcatctac tgcctatggg cccgccctga ccgggcgccc agctcctttg     300
ggcgccagca tcgacgctga cacgggcgcc atcaacttct cagtgttcag ctcctccgcc     360
gagtccgtga gcctggtgct gttcacggag gctgacctca cgcaggccg gccactttc      420 gagattcctc tggacccgta tgtgaaccgc acgggcgacg tgtggcacat catgctgccc     480
gacctgcggg acgacctgct gtacggctac cgtgtgcagg gcgtgcacca ggaggaggac     540
aaggactacc cgggcatgag gcacgacaag cggcgtgtgg ttctggaccc gtacgcggtg     600
gctgtgctca accggcggcg ctggggccag atggggccca actgccgta cggcgaggag      660 ggcgtgctgg cgtcatgcc cacgtggccg caggccgccg ccgcgctgcc cgccgcccgc     720
ggctccgcct tcgactggga gggcgacacg ccgctcaacc tgcccatgga gagcctggtc     780
atctacgagg cgcacgtgag gggcttcacg gcgcacgcca gcagcggggt ggcggcgccg     840
ggcacgtacg cgggcatggt ggagcggctg gactacctca gtcgctgggt gtgaacgcc      900 attgagctgc tgcccgtgtt cgagttcaac gagctcgagt actacagcca gatccccgga     960
agcgaccagt acaggttcaa cttctggggc tactccacgg tcaactactt cagccccatg    1020
ggccgcttca cgctgcggt gggccagggc gcgccggccc cgcctcctg cgacgagttc     1080 aagcagctgg tcaaggagtg ccacaggcgc ggcatcgagg tgatcctgga cgtggtgttc    1140
aaccatacgg ccgagggcaa cgagcgcggc ccaccatct ccttccgcgg cctggacaac     1200
cgcgtctact acatgctggc gccgggaggc gagtactaca actacagcgg ctgcggcaac    1260
```

| | |
|---|---|
| acgctcaact gcaaccagcc tgtggtgcgg cagttcatcc tggattgcct caagcactgg | 1320 |
| gtcaccgagt accacgtgga cgggttcagg ttcgacctgg cctccatcct gacccgcgcc | 1380 |
| cactcggcct ggcacccgca gcagtacgac caggagacgg ggcagcgcgt ggccatgagc | 1440 |
| agcggcggag ccatcgtcac agcggagggc atcatgactg acggtgcggg tgtgcccacc | 1500 |
| ggctacccgc tggccgaccc gcctctggtg gagtccatca gcgaggaccc cgtgctgcgg | 1560 |
| aacaccaaga tgatcgcgga ggcctgggac tgcgacggac tcaaccaggt cggcgccttc | 1620 |
| ccgcactacg gcggccgctg gagcgagtgg aacggcaagt ccgcgacgt ggttcgcaac | 1680 |
| ttcatcaagg gcacggacgg cccctgggcg ggcgacttcg cctccgccat ctgcggctcg | 1740 |
| cccaacatct acgccaacaa cacgccgcac gagaccgact ggtgggccaa caacggcggg | 1800 |
| cggcagtgga agggcggccg cggcccgcac gcctccatca acttcgtggc ggcgcatgac | 1860 |
| ggcttcacgc tggcagacat ggtggcctac aacaacaagc acaacgaggc caacggagag | 1920 |
| aacaaccggg acggcgagca acacaacaac agctggaact gcggcgagga ggggcccacc | 1980 |
| accaagtggg aggtcaaccg gctgcgtcag cgccagatgc gcaacctgac cggcgcgctg | 2040 |
| ctgctgtcgt gcggcgtgcc catgatcaac atgggcgacg agtacgggca cagcaagaac | 2100 |
| ggcaacaaca cacctactg ccacgacagc gagctaaact acctgcggtg ggaccagctg | 2160 |
| gccgaggacc cgcacggctt caaccgcttc gtgcgcctgc tgatccactt ccgccgcgcc | 2220 |
| acgcccgcgc tgcagcgcac caccttttgtc aacgacaagg acatccagtg gcacggcgag | 2280 |
| ctgcccaaca cgcccgactg gaccgacacc agccgcctgg tggccttcac gctgcacgac | 2340 |
| ggcaagggcg gcgccctgta cgtggccttc aacaccagcc acctgcccaa gctgctgcag | 2400 |
| ctgcccaagt ggggcggccg cgtgtggcag ccgctggtgg acaccagcaa ggtggccccc | 2460 |
| tacgacttcc tggcggtgga cggcgttctg agcgccgagg acgtgcggc ggcgcggcgg | 2520 |
| cagatggcca tgtggaccgc cgaccacacc taccccgtgc tgccctggag ctgcatcgtg | 2580 |
| ctgcagagcg cgcccgagga cccggccgcc acaagcatga tcaagtga | 2628 |

<210> SEQ ID NO 3
<211> LENGTH: 17329
<212> TYPE: DNA
<213> ORGANISM: Chlamydomonas reinhardtii
<220> FEATURE:
<221> NAME/KEY: misc_feature
<222> LOCATION: (13057)..(17091)
<223> OTHER INFORMATION: n is a, c, g, or t

<400> SEQUENCE: 3

| | |
|---|---|
| ggatcctgtc gatccggcat tgcatgggca tgttcgcatc aatcatgtgt ggattctccg | 60 |
| tgtcgggcct gatggcggtc cttggcccctt cacccacccg cgccttcaca cttgcccgca | 120 |
| ttgctccaaa ccaccacccc cggccccgcc acctgcgccg ccgcctgccc catgctactg | 180 |
| tgcctggcta tgccttcact tcttacatat gcatgaatgt aaccccaccc ctaacactgt | 240 |
| caggaagctg atccgtgact atcccaacct gtgcaactac gtgcgcgacc tgtaccacgt | 300 |
| gcccggcatc ggccgcaccg gtaggggcg gcggcgcgct ggaatgcaca aggggtgaac | 360 |
| ttgtgtgcgt atgatacagc tttgcgtgct tgctgtccat gtgctttcat acatgtgccg | 420 |
| cacacacaca cgccaacact gtcctgcgcg tatttctttc cttgcgcttt ttgaaaacac | 480 |
| gccaaacaca cccacttaca cgcacatact cgctcacacg cagttgacct gtaccacatc | 540 |
| aaggccgcct acttcacatg caaggtaggg cagggcagcg ccgggcaggg cagggcaggg | 600 |
| cagggcaggg cagggcaggg cagggcaggg cagggcaggg cagggcaggg cagggcaggg | 660 |

```
cagggcaggg cagggcaggg cagggcaggg gcgtcgcctg ctgtgtgcag cactcattga    720
ccgtgcccct gcccctttccc tgcgcccacc catctggcca ccaccccact gggcctccac    780
gcctgcctgc ttcccgtatc caataatttg ccaactatac cacatgtgtg cgtgttccgc    840
gcagcccgac atgaacccca acgtgatcat cccgggcggc ggcgacgcct ggtgggcaca    900
gccgcacgac cgcgctgaca agttcggggg caagcgcgag ggcggcgggc tggcgggctg    960
gctgcagaag ctgcccgtgt gggcgccgca cgccgccgcc tctgccgccg cggcgctggt   1020
ggcgggcgcg gcgctaggga gcagccggcg gcgctgagcg ggcgctgtgt atgtggaggt   1080
gtggttgcat gtttggatgt catttgtgtg aagtgcacca gtgatgcatt ttgtgcatgc   1140
atgcaaggcg gatgtgcatg tgtacacttc acggattgcg cgggttcttt cagggaatgg   1200
ccgaagcggg ggttgtcccg acatggctgc agccttcggg tgcggctgtt tgcgcaatgg   1260
cggtttgtcg gccggcgcgt acatctgaac atcaaaacgg aactcaaggt ctaggttgcg   1320
gtagcggatg aaaaaggcgt gggccgttta gttgcaaagc ggttcaggcg aacaggcgat   1380
tggggtggca gctgtgggtg gcagtccggg acagcccgac ggttatggtt cggcaccatg   1440
gcctcgacta attccaagcg cgtcagaagg gctgtgaatc ctgtcatgtt gtaactcgct   1500
tgacatgctg actgtgatgt gcactgtgct aaatgcatgc tgcatggagc ttgcttgcgt   1560
gccggttaga gtgcaaagcc atcgacggga gggaggcgtt gcacgcgcgc gtgtcaggtc   1620
agtcgcgcgt cggcggggtc aaccttgcag cctgcagcca actcaacccc ttttgcatcg   1680
actcatctca cggcgacccg ctattgcgac aaactgacga tcaggcagag cggtgcctgg   1740
gagacgactg gggacacgcc acgcacgggg aaatgccact tgacatcgtt tcaccgaact   1800
gtcaaagcgt ccctccgcat gacatgtctc caaccgaaaa tactcaatgc agttgacgtc   1860
cgtggcaggg aatggtagta gcagaggagg aggaggccag tcgtttccag ctccggtctg   1920
catggggcga atgttgcgtg cccccatgca gttcgcttga ccggggcgct aggcaaaccg   1980
gccttgcaaa gtcgcgcagt gtagcgctgc tcaatctgga agcgccttag caacaggcgc   2040
tagtcaacaa ccgcataccc ttgtgctgac gctggactgt gttagacttg ggtcttctct   2100
gaaccttgtg ttcccagctg agagtcgacg aatttcaata cttgctacgc attaatatcc   2160
aatttgggct cagccatgct tctgcaagcc cctggcctcg cgccgggctc ggctcgtcgc   2220
caggcagcct gcagcgtggc tcgcgaggca accaacgtgc gcattgtgac agcacctgct   2280
ttgacacccg ggcgcgctgg agtttctggc cggtgagcaa gcctcgcgat tctgcttttg   2340
gggtttagtt gcagctccct gtcgagcgct ttttgacggc gcgcttcaag caatctagtc   2400
gctagcccgc catgtctgta ctcttgcaca tcaagcctca atgcacgcgt ggggttgcgg   2460
gccaaacgga taacgcatgc tggaatatgt tgtgcgcggg ctggcaggcg tatcctcccg   2520
ccctcgcgcg tcgtgtccgt ggagctggag gccccgacgc tgtcgtcgag ccctgcgact   2580
gtcagcacca agaagttgtt ctgcgagccg agcgggcagc ccgcatctac tgcctatggg   2640
cccgccctga ccgggcgccc agctccttttg ggcgccagca tcgacgctga cacggtgagc   2700
gcgccatgca gctggaaact actcgatgtg gtcaacgttt ttggctgccc tcgacaactt   2760
cacaaaagtt ggttgcccgc cagtcgggtc ccctctcgtg cgctgggtgt tgcgcgcttt   2820
acctccaacc cgcacccggc cgcccgctcc tccaccgcct ccagcaccac acaccccaac   2880
gcacatttcc tcctacctca ctcactcctc tgcacgctcc tgcccagccc taccaaaccc   2940
acttcctgct cccatcttct ccaatcttcc gacagaatcc tacttgcgta acgttgctca   3000
```

```
cccccttttt cctacttcca tcagggcgcc atcaacttct cagtgttcag ctcctccgcc    3060
gagtccgtga gcctggtgct gttcacggag gctgacctca acgcaggccg ggccactttc    3120
gaggtgaggg aggggggcaga gggtggggtg gggtgggaaa ggtggttgag ggggtgcgaa    3180
agaggggtca ttcgtaccaa tccgaagtgg accaagaccc agcacaagcc cacgggtggg    3240
tttagaggga gctggcgtgg gggtggtaag tggtggcggt gaaggtgggt gaggcgggca    3300
gggtagccgg tgggagcggg tgtgttggta gtcatgttgt tgccggtgct gatgcgtgct    3360
ggcaggggca cctaacacac acgctcacgc acacgcccat attccgccgc cgcagattcc    3420
tctggacccg tatgtgaacc gcacgggcga cgtgtggcac atcatgctgc ccgacctgcg    3480
ggacgacctg ctgtacggtg agatgactgg ggggggattt gggggaaagg cagtgaggag    3540
gataactctc ccctgaaaaa gcagcgcagc aaggagaagc tgcagccgca tatgcgggtg    3600
cagcggggtg gtatgggccc gagcccaaca cattatagga agcagcggtg gcggtgggaa    3660
ggagcgagca gggggaggag gtttggggag aggggccgaa ggcaggggag ggagcaggca    3720
gggctagagg ggttggggcg tgaggagcg gggaggcaga ggggtgtacc tggcggggtg    3780
aggtggcagg gctcggctgg ggcaggagga agcgggtagg cgggcggtgg gaggcggtgt    3840
ggagggcctg cggtcccgga catggcgtg tgggagctga cggccaggga gggggcaggc    3900
gcacgcgggg cgggtggggg gcaggggcag gggcggtagg ggcttgggca gcagctgcca    3960
agggatgagt cgtctgcccc accaaggagc agacggcggc aagcgaagta tgcctgaaga    4020
ggacgcgagg cgcccaccta ccgcctcctc ctccctctcc ctagccctca cccgaaccct    4080
ctcacccgaa cccctcctca cctctcctgc tcctctcctc cctccccct ccctccaggc    4140
taccgtgtgg agggcgtgca ccaggaggag gacaaggact acccgggcat gaggcacgac    4200
aaggtgtgtg tgtgtgtggt gtgtgtgtgt gtgtgtgtgt gtgtgtgtgt gtgacaaggt    4260
gtgctcgggt gtgggctcaa acaagtgggc gtcgtaacgg gctgggtgta acatttggtg    4320
tgacaggaaa ggtacgggac taccgtacat cgctcgcgac ctcggcccac ccacccatcc    4380
gttcatccat gcactaccgg taatccctct ctccgcttcc ccccttcccc ctctcccgcc    4440
cacccccctc cagcggcgtg tggttctgga cccgtacgcg gtggctgtgc tcaaccggcg    4500
gcgctggggc cagatggggc ccaacctgcc gtacggcgag gagggcgtgc tgggcgtcat    4560
gcccacgtgg ccgcaggtgg gtgggccgtg gagggcgcgg cgtgggccgt gctgtactgt    4620
ggagaggttg agagggctgg gggcggggcg gggcggggat ggggatgggg atggggttga    4680
agaggagctt gtgggactgg cttgtgccag cggcacggcg gcaggccacg gcctgagctg    4740
gtctgaccca cgtgcacatt gcgctttcgc aacgccacat gcacacatgc acgtgccccc    4800
caccaccacc gcaggccgcc gccgcgctgc ccgccgcccg cggctccgcc ttcgactggg    4860
agggcgacac gccgctcaac ctgcccatgg agagcctggt catctacgag gcgcacgtga    4920
ggggcttcac ggcgcacgcc agcagcgggg tggcggcgcc gggtgagcgg caggcggagg    4980
gggtggggag gggaggggag cggggcttgg ggtgcggggg gtgggtgggg gccagggtgc    5040
aaggtggagg cgcgctaggg ctacaagctt gggggcggg gggcggggtt ggggaggtag    5100
gggaagaggt gcgggcggc cgcgggcggg gtggccagag acaggaaatg agaaggagg    5160
aggcgtggca agttgggctc cagggcctta gagaggcaag cccacttacc gcccgccccc    5220
actcctcctc acctcctccc accccctgcc taggcacgta cgcgggcatg gtggagcggc    5280
tggactacct caagtcgctg ggtgtgaacg ccattgagct gctgcccgtg ttcgagttca    5340
acgagctcga gtactacagc cagatccccg gaagcgacca gtacaggtga ggggaaggg    5400
```

```
gggggggtata tgaccgagcc caacgaatgg gggttggaga gggtgcgggg cagccgacac   5460
cagatcccag taaacgggcg cttggcatag cccgcggtga aagcgctggc tcgcgggggt   5520
ctccttgctg ggggtcatct tgcgaggggc tgaagggagc gctatggaat atcctggcat   5580
accacctcat ccccccttg tgggcctctc cccatcacc cccatcacca cctcacacac    5640
ccctcacaca ccctcatcc aggttcaact tctgggcta ctccacggtc aactacttca    5700
gccccatggg ccgcttcagc gctgcggtgg gccaggcgc gccggcccgc gcctcctgcg   5760
acgagttcaa gcagctggtc aaggagtgcc acaggcgcgg catcgaggtg agcaggctgg   5820
gagggggcgg gggtggataa tgaagggagg tgggggcggg agaggcgcc gaggctggcg   5880
ttggcgtgtg tacgtcctgt tctggactct ttccacccct cctgacctgc taccgccaac   5940
ggctgccaca ccactgcctc ccccccaccg ccgttatata caaccttct ggaaacccct   6000
ccgtccaccc catcaacggc tcccctact gcccctcctg cccttcccc cctgccccc     6060
ctcaggtgat cctggacgtg tgttcaacc atacggccga gggcaacgag cgcggccca    6120
ccatctcctt ccgcggcctg acaaccgcg tctactacat gctggcgccg ggaggcgagt   6180
actacaacta caggtggggg ggagggctgg gggggaggg ctggggggg agggctgggg    6240
ggggagggc tggggggggg agggcgggg aagggaaggt ggggcaaggg taaggggagg    6300
ggatgggatg ggagggcatg gtggggaggg gagggaggg gtaaagggag gggtaagggg   6360
accgccgtgc attatgcatg ctgtatcgag ggtgatgtag tggtatgcag ggggggaagg   6420
gtggagggga gaagtggctc agaagcagtg cagggctcac aggggttgtt ggggcaaggg   6480
gggaggatgg gcgcgttggg agcaaggggg cagcagaggg gccgtgttgc gtggaacagg   6540
ggcagggcgg ggcggtgttc gggggcaagg ggcggatggg acaaagcagc tctcgctcgc   6600
cctgcacact gcactgggc gtgccggcaa gtgcctcccg cgcctcggtc cccccaccag   6660
tcatgccccc atcctcaccg cccgcccac cttacctgcc cccacccta ccatgtcccc    6720
gcagcggctg cggcaacacg ctcaactgca accagcctgt ggtgcggcag ttcatcctgg   6780
attgcctcaa gcactgggtc accgagtacc acgtggacgg gttcaggtgg ggaggagggg   6840
aggggaggaa ggagggagg aggacaggtt gcaggggccg ggcggtgggc ggggcgggcc   6900
tgaccggggg gataccggcg gattcggggg ataccgggca taagaaatga gagcgtgcga   6960
gtgcgtcccc ttcatcacca ggctgtgctt ccgccacttg catctggatc ggaaacctgc   7020
tcttgtgccc acctctcccc tctccctct cccgtctacc cccgccaggt tcgacctggc    7080
ctccatcctc acccgcgccc actcggcctg gcacccgcag cagtacgacc aggagacggg   7140
gcagcgcgtg gccatgagca gcggcggagc catcgtcaca gcggagggtg ggtgggaggc   7200
aggcggggg tggtggggca gggaagaggg tgaaagaaag ggggtttaca ccaccgctgg    7260
aggcggggga aggaggttga attgcgaggt ggaaagggag gcaaatgcag tgagagcgaa   7320
acccaatgtg agcggtgctg catctgcggg ctgccggggg gggctgtgc tcgtgaaagg    7380
tctagccacc gcactcccac acgctctctc ccttcctctc cctttccctg tcgcctatgc   7440
ctgtgttccg ctggcttggc tcggtttggt ttagttttgg ctggtactta caactcccta   7500
cacgcacacg cacacacgta cgcaggcatc atgactgacg gtgcgggtgt gcccaccggc   7560
taccgctgg ccgacccgcc tctggtggag tccatcagcg aggacccgt gctgcggaac     7620
accaagatga tcgcggaggc ctgggactgc gacggactca accaggtggg gtcgggggga   7680
agggggtagg tattcacgat aaatcaagaa caagcgggtt taataggggg cgcgtgtagg   7740
```

-continued

```
ggtgctcgaa gtgtgtgtgc gtgtgctaga tagcagtagg caaacgttgg aatcagtgtg    7800
tcctaatctt ggtgttcgct gccaccgccc cgatcaaccc aggtcggcgc cttcccgcac    7860
tacggcggcc gctggagcga gtggaacggt gggtgggtgc tgacgtcagc acacgtgtcc    7920
gggcgtgttc agagacaaca ggcacggcgc gagctgcggg gagggggcac ttgtggggta    7980
tttcacgtgg agagagaagg aggcgcagct gacgtggtca tacctgagcg atgtggccgg    8040
gggctgggct taccaaatcg cgatgccaac acacatgctt accacaaaca cacgtgcagg    8100
caagttccgc gacgtggttc gcaacttcat caagggcacg gacggcccct gggcgggcga    8160
cttcgcctcc gccatctgcg gctcgcccaa catctacgcc aacaacacgc cgcacgagac    8220
cgactggtga gcagcgggca cgggggggtgg ggcgatgcgg tggacgagcg ggggggggga    8280
ggagggtgca ggagggcacg gggggtgctgt cggtgcgacc ggcattagtg tttggggaga    8340
tgggtattgc ttggggcagg agtcagccgg gcagtgttcg ttcagtgcgt tgtcaagatt    8400
tgtagatgtg acaggactgt gagcgagcgc gtgttcgtgg tcgtgatgag acgacacgtg    8460
cgggcgctgt gtgacgtgtg gtgcgggcgc acgcaggtgg gccaacaacg gcgggcggca    8520
gtggaagggc ggccgcggcc cgcacgcctc catcaacttc gtggcggcgc atgacggctt    8580
cacgctggca gacatggtgc gtgtagggtc cggggggggg ggcggagaaa ggcggggggaa    8640 ggcaggggag ggaaagggcg gcggcagcgg gggaggccgg aaagagtgtt gaggcgagcg    8700
ggagggaagc gaatgctggc gctggcagtg aaggcactga tgatgcgatg gaatggcatg    8760
caggcagcag ccgtgtgtac agtgctgcgt catacagggt gctcagtcgt acataatggg    8820
cccaaccgac cgaccgtctg acgcaaccgt gtgtggcgcc cccccccctg caggtggcct    8880
acaacaacaa gcacaacgag gccaacggag agaacaaccg ggacggcgag caacacaaca    8940
acagctggaa ctgcggcgag gaggggccca ccaccaagtg ggaggtcaac gtgagtcatt    9000
tgattagggt gctgcgtgtg tatgcaggtg ctgtgcaggg aggaggagga ggaggggaa    9060 gctccacgct gctcgcctga tggcaccttc ctgcacacct ctatccccgc gtccgctgcc    9120
ccgcaccctt atccccgccg ccgcctccac tcccccactg ctcttaatta atcatgaatg    9180 taattccca ctgcccccct tccccttac cacttcctca actaatcatg aatgtaaccc    9240
ccacacacac gcagcggctg cgtcagcgcc agatgcgcaa cctgaccggc gcgctgctgc    9300
tgtcgtgcgg cgtgcccatg atcaacatgg gcgacgagta cgggcacagc aagaacggca    9360
acaacaacac ctactgccac gacagcgagc taaactacct gcggtgagcc cagcggcgat    9420
ctcggcaatc ctttgtgttc tcaaccctgg tgccgtttgg ttatgcgtgg tgtgcacacc    9480
ttcagtcgga cacgaaatct ttccccggat gcgccgctct tacacctctc tacccgacac    9540
ctccaccgcc gcctcctcgc aggtgggacc agctggccga ggacccgcac ggcttcaacc    9600
gcttcgtgcg cctgctgatc cacttccgcc gcgccacgcc cgcgctgcag cgcaccacct    9660
ttgtcaacga caaggacatc cagtggcacg gcgaggtgcg cggcatgggc cttggacttg    9720
ggggtgggag tggcgcgggg cctggatgga gcttattggg gggggggcgt ggggaggaa    9780 gtggtgggtg accaggagat gctctgaata cgaacatgag cgagctgcat ggggattgg    9840 gggcaccgag caaggcgtga tgcatatcgc cccctggctt ggccggactg tcccttcttg    9900
tcatgttgca tgcatatcgc cgcccccacc tggtgttccc ctccgcttcc ctcactacgc    9960
aaccccctac cgccccccc cccccgcag ctgcccaaca cgcccgactg gaccgacacc    10020
agccgcctgg tggccttcac gctgcacgac ggcaagggcg gcggcctgta cgtgccttc    10080 aacaccagcc acctgcccaa gctgctgcag ctgcccaagt ggggcggccg cgtgtggcag    10140
```

```
ccgctggtgg acaccagcaa ggtgcgggcc tgaggggaaa gaggaggaa gaggagggg    10200
agggctgcgc ggagaggcgc atgccggtgt gtgcctggag cgacctttct atcagctcat   10260
cgctgtcgtc acctcattcc gttccattac cgtgtcgttc acacacacgc cccacgtaaa   10320
cacatgccgg ccatgtgaac gcacacgcag gtggccccct acgacttcct ggcggtggac   10380
ggcgttctga gcgccgagga cgtggcggcg gcgcggcggc agatggccat gtggaccgcc   10440
gaccacacct accccgtgct gccctggagc tgcatcgtgc tgcagagcgc gcccgaggac   10500
ccggccgcca caagcatgat caagtgaggg ggagggaggc agaggagg gggaaaggga   10560
ggagcgggtt ccatggaggc tagtcgtgtg tatctgtcgc tgccccttgt ggaacatggg   10620
taaggcccgc tcagcaagag cactgccgcc gccgccacct gccacacgct catcgccttg   10680
tgctcttccc ctgccctccc ctgccccggc cgacaggcgc gccgcccagc gctccggccc   10740
cgcgcccgcc tccggcccca gcggccccgc caaccccatg acctgggcca ccaacttcat   10800
cagcggacag gtgcggcgcc tcgtgtcggt gcgtggcggc agtgtggtgc gtgaccgcat   10860
cgtgcgctag gagctatgcg gaagagagtc tcgacaccgg gcccccgcca tgcgactgtg   10920
ttgatgcatt cgacgcctag cttcctgtgg ccctgtcat gtgctgcttt ataactcacg   10980
tgtggaacgt atcatgcgtg tcatcctgcg gctgcctccc tcggcccac agccgcccac   11040
acccggcaac ggccccgcg gcggcgccag cggctcatcc tcctacggcg gcgcgtacgg   11100
cgccgcacag accgcgtacg gcagcaacgg caacggcgcc aacgtgatcg gctcctacgg   11160
accgccgcc accgccacca cctcctcctc cccggcggcg cgccgcgt ccgccgccgt   11220
cgccggcagc agccgcagcg ccagcgcgcc gcgcgccgcg cccgcggccc ccgcccactc   11280
caacaacgcc cacgtgcttc ctcctcccgc cgccgcctcc acggggtcag gctccaaccg   11340
ctccaactgg cgcgcaatgc tggacgagca gccgccggca gctgctgctg ctgctgcggc   11400
ggcggcggcg gcggcggctg ggtcgtggca gctgtcgtct ctggcctcgg cggacagcga   11460
caacgagggc atgacggcgg cggagcgggc ggcgctggag caggccatgc gcgagaacga   11520
ggcgctgagg aagcggctgg ggctgtaggg ggctgcaggc atctgcaggc agccgggggg   11580
ctgtggggct gcaggccgtt acaccggtgc tatgcagtga ggagagaagg gcagaagcgg   11640
gagatgggag cgggtggagg gatgaagggg cggggtggg tggaggaggc gctgcagggg   11700
cagagagtcg ctgctggcgg cggtgttgag aggcggcgtg agcagcgggt gggtgggtag   11760
aggtagggcg gggcaccggc gttggaggaa gagcgggaag agctgctgca agtgccgccg   11820
ccgcgataac tgtgtcatgg tcccaggtgc aagaccacaa gttgtgaacg aagaatgaat   11880
aagttctttg gtgttgttga cgcgcccacg cccgagcaaa acacgggcgg gggctgtgtc   11940
tagagcctga gcgttacatg ctcttgcgtt ctttggcact cacacttgct cgcatgggag   12000
agctaagttt gcagacatgt cgtttgcaca ttttcttgga gccagctcta cgccttggcc   12060
tcattttgag tgcgggtgag tgtgcggttg gggttgtagc gtcggtttg gtcatcgacc   12120
cctcggcact gtgcatgagt tgaatgctgg atacgagatc atgtcgcaaa gttttggttt   12180
gacagggtgt tgagcaacga atctggagag gtggggcgc ggcgatggcg cgttgtgtgg   12240
gttttcccct ggccgtgccg gcatgagaga gagaacagct tgctgtgcac actgctaggg   12300
gcgccacagt aggttatgcc ctgcacatat cagtaccgcc tggcaacggt ttagaacacc   12360
ttggaaggca aaaccacag agggactggc attgcaatcc cgatgggttg atgttgtcat   12420
tgacgctggt ccgtcggtgg atgcagagcc caggcgagag agggggttgc ggccgagggc   12480
```

-continued

```
ggcagcgtgt gcgctgcgtt gagcgtaccc caaagcgctt tggcgcaagc aaaccgagcg    12540
tcctgcacgg agagactgag tcctgagaga gccaagtttg gttgcggcac tgaggaagaa    12600
cgaatgcgag cagtgtgaac agtgtctccc ccatgggagc tggcgcgttg aaacatgaga    12660
gcgcacccta gtgccgagtg ccattgagcg tgttggtagg ggtttacggg tcattgcctg    12720
cgtggccctg tcgttccacg tgttgacaag gttgttcgtg ttcctagtct ttgaccattg    12780
tttcggtagc tatgcattgg cggcttagaa cggcaactcg attgcggcta ggaactgcta    12840
gtattacggt agtacgacag cgggggccga gtaggttcga gaactggaca ggttggcagg    12900
tgcgcgtgcc aagcgccaca tgtgccccgt gctgctgctg ctcgccaccg ccttggttgg    12960
cgtggcagcg gctgagtggg gcgggtgtgg gctggtggct gccctggcgg cgttgggacc    13020
atactcgtgt aacactaaaa gcagcgcggc acgtccnnnn nnnnnnnnnn nnnnnnnnnn    13080
nnnnnnnnnn nnnnnnnnnn nnnnnnnnnn nnnnnnnnnn nnnnnnnnnn nnnnnnnnnn    13140
nnnnnnnnnn nnnnnnnnnn nnnnnnnnnn nnnnnnnnnn nnnnnnnnnn nnnnnnnnnn    13200
nnnnnnnnnn nnnnnnnnnn nnnnnnnnnn nnnnnnnnnn nnnnnnnnnn nnnnnnnnnn    13260
nnnnnnnnnn nnnnnnnnnn nnnnnnnnnn nnnnnnnnnn nnnnnnnnnn nnnnnnnnnn    13320
nnnnnnnnnn nnnnnnnnnn nnnnnnnnnn nnnnnnnnnn nnnnnnnnnn nnnnnnnnnn    13380
nnnnnnnnnn nnnnnnnnnn nnnnnnnnnn nnnnnnnnnn nnnnnnnnnn nnnnnnnnnn    13440
nnnnnnnnnn nnnnnnnnnn nnnnnnnnnn nnnnnnnnnn nnnnnnnnnn nnnnnnnnnn    13500
nnnnnnnnnn nnnnnnnnnn nnnnnnnnnn nnnnnnnnnn nnnnnnnnnn nnnnnnnnnn    13560
nnnnnnnnnn nnnnnnnnnn nnnnnnnnnn nnnnnnnnnn nnnnnnnnnn nnnnnnnnnn    13620
nnnnnnnnnn nnnnnnnnnn nnnnnnnnnn nnnnnnnnnn nnnnnnnnnn nnnnnnnnnn    13680
nnnnnnnnnn nnnnnnnnnn nnnnnnnnnn nnnnnnnnnn nnnnnnnnnn nnnnnnnnnn    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnnn nnnnnnnnnn    14100
nnnnnnnnnn nnnnnnnnnn nnnnnnnnnn nnnnnnnnnn nnnnnnnnnn nnnnnnnnnn    14160
nnnnnnnnnn nnnnnnnnnn nnnnnnnnnn nnnnnnnnnn nnnnnnnnnn nnnnnnnnnn    14220
nnnnnnnnnn nnnnnnnnnn nnnnnnnnnn nnnnnnnnnn nnnnnnnnnn nnnnnnnnnn    14280
nnnnnnnnnn nnnnnnnnnn nnnnnnnnnn nnnnnnnnnn nnnnnnnnnn nnnnnnnnnn    14340
nnnnnnnnnn nnnnnnnnnn nnnnnnnnnn nnnnnnnnnn nnnnnnnnnn nnnnnnnnnn    14400
nnnnnnnnnn nnnnnnnnnn nnnnnnnnnn nnnnnnnnnn nnnnnnnnnn nnnnnnnnnn    14460
nnnnnnnnnn nnnnnnnnnn nnnnnnnnnn nnnnnnnnnn nnnnnnnnnn nnnnnnnnnn    14520
nnnnnnnnnn nnnnnnnnnn nnnnnnnnnn nnnnnnnnnn nnnnnnnnnn nnnnnnnnnn    14580
nnnnnnnnnn nnnnnnnnnn nnnnnnnnnn nnnnnnnnnn nnnnnnnnnn nnnnnnnnnn    14640
nnnnnnnnnn nnnnnnnnnn nnnnnnnnnn nnnnnnnnnn nnnnnnnnnn nnnnnnnnnn    14700
nnnnnnnnnn nnnnnnnnnn nnnnnnnnnn nnnnnnnnnn nnnnnnnnnn nnnnnnnnnn    14760
nnnnnnnnnn nnnnnnnnnn nnnnnnnnnn nnnnnnnnnn nnnnnnnnnn nnnnnnnnnn    14820
nnnnnnnnnn nnnnnnnnnn nnnnnnnnnn nnnnnnnnnn nnnnnnnnnn nnnnnnnnnn    14880
```

```
nnnnnnnnnn nnnnnnnnnn nnnnnnnnnn nnnnnnnnnn nnnnnnnnnn nnnnnnnnnn    14940
nnnnnnnnnn nnnnnnnnnn nnnnnnnnnn nnnnnnnnnn nnnnnnnnnn nnnnnnnnnn    15000
nnnnnnnnnn nnnnnnnnnn nnnnnnnnnn nnnnnnnnnn nnnnnnnnnn nnnnnnnnnn    15060
nnnnnnnnnn nnnnnnnnnn nnnnnnnnnn nnnnnnnnnn nnnnnnnnnn nnnnnnnnnn    15120
nnnnnnnnnn nnnnnnnnnn nnnnnnnnnn nnnnnnnnnn nnnnnnnnnn nnnnnnnnnn    15180
nnnnnnnnnn nnnnnnnnnn nnnnnnnnnn nnnnnnnnnn nnnnnnnnnn nnnnnnnnnn    15240
nnnnnnnnnn nnnnnnnnnn nnnnnnnnnn nnnnnnnnnn nnnnnnnnnn nnnnnnnnnn    15300
nnnnnnnnnn nnnnnnnnnn nnnnnnnnnn nnnnnnnnnn nnnnnnnnnn nnnnnnnnnn    15360
nnnnnnnnnn nnnnnnnnnn nnnnnnnnnn nnnnnnnnnn nnnnnnnnnn nnnnnnnnnn    15420
nnnnnnnnnn nnnnnnnnnn nnnnnnnnnn nnnnnnnnnn nnnnnnnnnn nnnnnnnnnn    15480
nnnnnnnnnn nnnnnnnnnn nnnnnnnnnn nnnnnnnnnn nnnnnnnnnn nnnnnnnnnn    15540
nnnnnnnnnn nnnnnnnnnn nnnnnnnnnn nnnnnnnnnn nnnnnnnnnn nnnnnnnnnn    15600
nnnnnnnnnn nnnnnnnnnn nnnnnnnnnn nnnnnnnnnn nnnnnnnnnn nnnnnnnnnn    15660
nnnnnnnnnn nnnnnnnnnn nnnnnnnnnn nnnnnnnnnn nnnnnnnnnn nnnnnnnnnn    15720
nnnnnnnnnn nnnnnnnnnn nnnnnnnnnn nnnnnnnnnn nnnnnnnnnn nnnnnnnnnn    15780
nnnnnnnnnn nnnnnnnnnn nnnnnnnnnn nnnnnnnnnn nnnnnnnnnn nnnnnnnnnn    15840
nnnnnnnnnn nnnnnnnnnn nnnnnnnnnn nnnnnnnnnn nnnnnnnnnn nnnnnnnnnn    15900
nnnnnnnnnn nnnnnnnnnn nnnnnnnnnn nnnnnnnnnn nnnnnnnnnn nnnnnnnnnn    15960
nnnnnnnnnn nnnnnnnnnn nnnnnnnnnn nnnnnnnnnn nnnnnnnnnn nnnnnnnnnn    16020
nnnnnnnnnn nnnnnnnnnn nnnnnnnnnn nnnnnnnnnn nnnnnnnnnn nnnnnnnnnn    16080
nnnnnnnnnn nnnnnnnnnn nnnnnnnnnn nnnnnnnnnn nnnnnnnnnn nnnnnnnnnn    16140
nnnnnnnnnn nnnnnnnnnn nnnnnnnnnn nnnnnnnnnn nnnnnnnnnn nnnnnnnnnn    16200
nnnnnnnnnn nnnnnnnnnn nnnnnnnnnn nnnnnnnnnn nnnnnnnnnn nnnnnnnnnn    16260
nnnnnnnnnn nnnnnnnnnn nnnnnnnnnn nnnnnnnnnn nnnnnnnnnn nnnnnnnnnn    16320
nnnnnnnnnn nnnnnnnnnn nnnnnnnnnn nnnnnnnnnn nnnnnnnnnn nnnnnnnnnn    16380
nnnnnnnnnn nnnnnnnnnn nnnnnnnnnn nnnnnnnnnn nnnnnnnnnn nnnnnnnnnn    16440
nnnnnnnnnn nnnnnnnnnn nnnnnnnnnn nnnnnnnnnn nnnnnnnnnn nnnnnnnnnn    16500
nnnnnnnnnn nnnnnnnnnn nnnnnnnnnn nnnnnnnnnn nnnnnnnnnn nnnnnnnnnn    16560
nnnnnnnnnn nnnnnnnnnn nnnnnnnnnn nnnnnnnnnn nnnnnnnnnn nnnnnnnnnn    16620
nnnnnnnnnn nnnnnnnnnn nnnnnnnnnn nnnnnnnnnn nnnnnnnnnn nnnnnnnnnn    16680
nnnnnnnnnn nnnnnnnnnn nnnnnnnnnn nnnnnnnnnn nnnnnnnnnn nnnnnnnnnn    16740
nnnnnnnnnn nnnnnnnnnn nnnnnnnnnn nnnnnnnnnn nnnnnnnnnn nnnnnnnnnn    16800
nnnnnnnnnn nnnnnnnnnn nnnnnnnnnn nnnnnnnnnn nnnnnnnnnn nnnnnnnnnn    16860
nnnnnnnnnn nnnnnnnnnn nnnnnnnnnn nnnnnnnnnn nnnnnnnnnn nnnnnnnnnn    16920
nnnnnnnnnn nnnnnnnnnn nnnnnnnnnn nnnnnnnnnn nnnnnnnnnn nnnnnnnnnn    16980
nnnnnnnnnn nnnnnnnnnn nnnnnnnnnn nnnnnnnnnn nnnnnnnnnn nnnnnnnnnn    17040
nnnnnnnnnn nnnnnnnnnn nnnnnnnnnn nnnnnnnnnn nnnnnnnnnn nagctggcgc    17100
acgaacggct gcagcgggca ggcggaggca gtagggcgg ggggttgcaa acatggttga     17160
attaacagga tgcactgaag gggaggggtt tgcaaatacc agcccaaact aaaccaaacc    17220
```

```
aagtcaaact tggtttggtt gccaaacttg gcaggggcag gcaggcagag ctgttcaaga    17280
ggcgggagag cgtggcctgc cgtgtcagtc tgctcccaca ccaggtacc               17329
```

MODIFIED ALGAE FOR IMPROVED BIOFUEL PRODUCTIVITY

CROSS REFERENCE TO RELATED APPLICATIONS

This application claims benefit of priority pursuant to 35 U.S.C. §119(e) of U.S. provisional patent application No. 61/467,919 filed 25 Mar. 2011, which is hereby incorporated herein by reference in its entirety.

STATEMENT REGARDING RESEARCH & DEVELOPMENT

Described examples were made with Government support under Grant No. FA9550-05-1-0365 awarded by the Air Force Office of Scientific Research. The Government may have certain rights in this invention.

FIELD

The disclosed processes, methods, and systems are directed to lipid and starch production from a modified algae.

BACKGROUND

Microalgae are able to efficiently convert sunlight, water, and $CO_2$ into a variety of products suitable for renewable energy applications including $H_2$, carbohydrates, and lipids. The unicellular green alga *Chlamydomonas reinhardtii* has emerged as a model organism for studying algal physiology, photosynthesis, metabolism, nutrient stress, and the synthesis of bioenergy carriers. During acclimation to nitrogen deprivation, *C. reinhardtii* cells accumulate significant quantities of starch and form lipid bodies. Despite the significance of these products in algal physiology and in biofuels applications, the metabolic, enzymatic, and regulatory mechanisms controlling the partitioning of metabolites into these distinct carbon stores are poorly understood in algae.

What is needed is a modified algae that can produce large quantities lipid and/or starch and methods of producing the same from modified algae.

SUMMARY

Disclosed herein are modified algae and methods of producing starch from modified algae. In one embodiment, a modified algae is disclosed comprising an isoamylase gene that is over-expressed in the modified algae compared to isoamylase in an unmodified algae, wherein synthesis of starch by the modified algae is increased relative to the unmodified algae. In some embodiments, the modified algae comprises one or more copies of an isoamylase expression construct. In another embodiment, a modified algae is disclosed comprising a mutated isoamylase gene; and one or more copies of an isoamylase expression construct; wherein synthesis of starch by the modified algae is increased relative to the unmodified algae. In some embodiments, the isoamylase expression construct is a genomic copy of the isoamylase gene, which is from the same genus of algae as the modified algae. In some embodiments the isoamylase expression construct is integrated into the algal genome. In many embodiments the modified algae is a starch producing algae, for example a green or red algae. In some embodiments the modified algae is *Chlamydomonas reinhardtii*. In some embodiments, the *Chlamydomonas reinhardtii* is a sta7 mutant algae. In some embodiments the *Chlamydomonas reinhardtii* sta7 comprises one or more copies of an isoamylase expression construct comprising a *Chlamydomonas reinhardtii* genomic isoamylase coding sequence; wherein synthesis of starch by the modified algae is increased relative to the unmodified algae.

Disclosed herein are methods of producing starch from a modified algae comprising: growing a modified algae in a growth medium, wherein the modified algae comprises an isoamylase gene that is over-expressed compared to an unmodified algae, wherein synthesis of starch by the modified algae is increased relative to the unmodified algae; isolating the modified algae from the growth medium; and processing the algae to produce a starch. Also disclosed herein are methods of producing starch from a modified algae comprising: growing a modified algae in a growth medium, wherein the modified algae comprises a mutated isoamylase gene; and one or more copies of an un-mutated isoamylase expression construct; wherein synthesis of starch by the modified algae is increased relative to the unmodified algae; isolating the algae from a growth medium; and processing the algae to produce a starch.

While multiple embodiments are disclosed, still other embodiments of the present invention will become apparent to those skilled in the art from the following detailed description. As will be apparent, the invention is capable of various modifications, all without departing from the spirit and scope of the present invention. Accordingly, the detailed description is to be regarded as illustrative in nature and not restrictive.

BRIEF DESCRIPTION OF THE DRAWINGS

(FIG. 2A) Starch-derived glucose per million cells. (FIG. 2B) Starch-derived glucose per milliliter of culture. Starch levels were analyzed after 28 h in CC124, c5, and c19 to determine whether maximum accumulation was reached prior to 96 h. Each data point represents five replicates. (FIG. 2C) Verification of starch phenotype in CC124, sta6, and sta7. Cells were spotted on TAP and TAP-N agar plates, as indicated. After 7 days the cells were imaged on TAP plates and the TAP-N plate was stained with iodine vapors and imaged (far right) to indicate the presence of starch (deep purple color).

(FIG. 3A) Lipid quantified per million cells. (FIG. 3B) Lipid quantified by milliliter of culture.

(FIG. 5A) Concentrations of acetate remaining in CC124, sta6, sta7, and two sta7 complemented strains (sta7: STA7), c5 and c19, in TAP-N medium at indicated culturing times. Cultures were inoculated at approximately $2.0-2.5 \times 10^6$ cells/ml. Initial acetate concentration in TAP and TAP-N media is 17.5 mM. Values are representative of triplicate biological samples. (FIG. 5B) Oxygen evolution from 0.8 ml aliquots of indicated strains after 24 h in nitrogen-depleted TAP-N medium. Oxygen evolution is shown from left to right on the basis of culture volume, cell number, and chlorophyll, respectively. Cultures were inoculated at approximately $1.0 \times 10^7$ cells/ml to produce $O_2$ at levels sufficient for detection.

DETAILED DESCRIPTION

Figure 1:
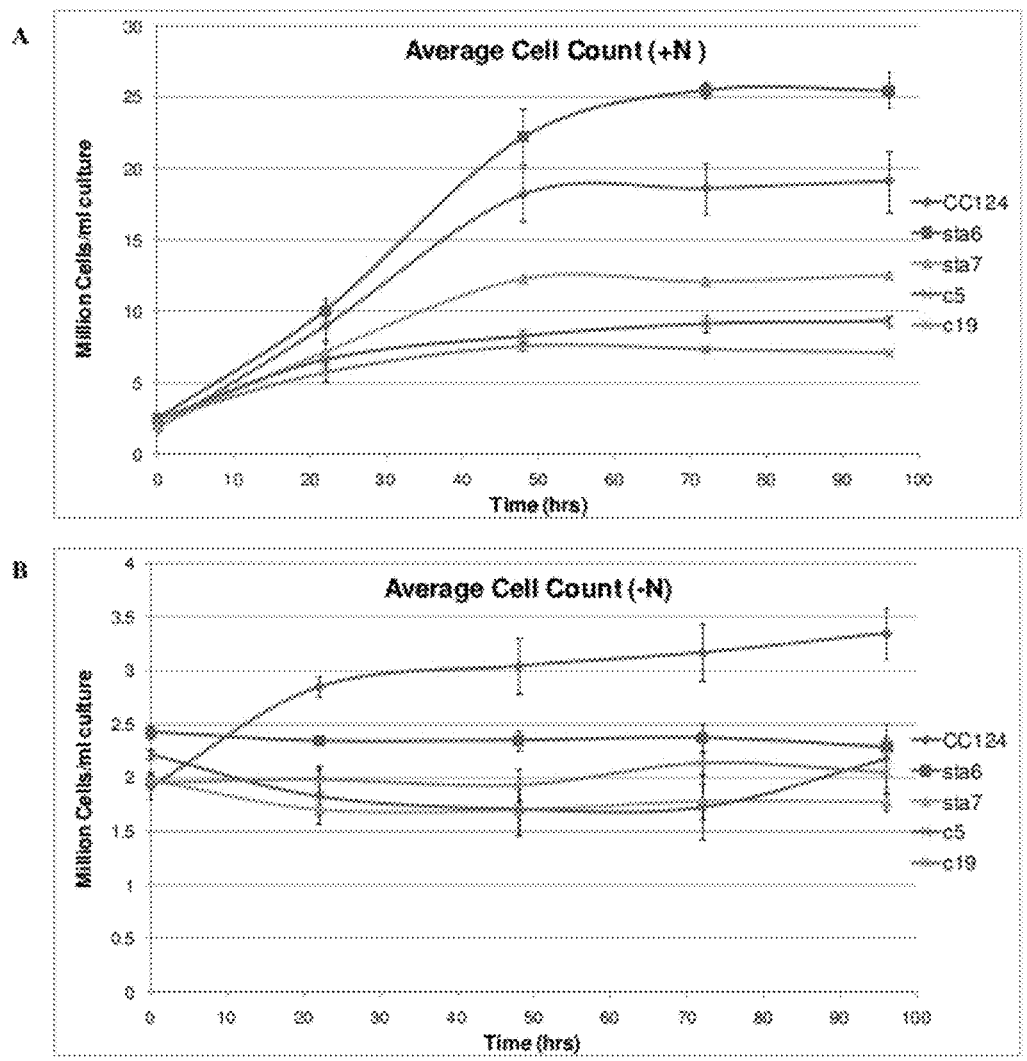
FIG. 1. Cell counts for CC124, sta6, sta7, and two sta7:STA7 complemented strains, c5 and c19. Growth curves from a representative experiment are shown and were constructed from cell counts at resuspension (0h) until 96 h, as indicated, in (FIG. 1A) TAP or (FIG. 1B) nitrogen-depleted TAP-N media. Each data point represents three replicates, except for c5, which represents 2 biological replicates.

Disclosed herein are modified algae and methods of producing starch from modified algae, wherein the modified algae over-express isoamylase relative to an unmodified, or wild-type algae. In one embodiment, a modified algae is disclosed comprising an isoamylase gene construct, wherein synthesis of starch by the modified algae is increased relative to the unmodified algae. In some embodiments, the isoamylase expression construct comprises a genomic isoamylase gene. In some embodiments, the modified algae is a wild-type algae comprising one or more copies of an isoamylase expression construct.

Also disclosed herein, is a modified algae comprising a mutated isoamylase gene; and one or more copies of an un-mutated isoamylase expression construct; wherein synthesis of starch by the modified algae is increased relative to the unmodified algae. In some embodiments, the un-mutated isoamylase expression construct may comprise a genomic copy of the isoamylase gene, which may be from the same algae or other sources, the isoamylase expression construct may be integrated into the algal genome. In many embodiments the modified algae is a starch producing algae, for example a green or red algae. In some embodiments the modified algae is *Chlamydomonas reinhardtii*. In some embodiments, the *Chlamydomonas reinhardtii* is a sta7 mutant algae. In some embodiments the *Chlamydomonas reinhardtii* sta7 comprises one or more copies of an isoamylase expression construct comprising a *Chlamydomonas reinhardtii* genomic isoamylase coding sequence; wherein synthesis of starch by the modified algae is increased relative to the unmodified algae.

Disclosed herein are methods of producing starch from a modified algae comprising: growing a modified algae in a growth medium, wherein the modified algae comprises an isoamylase gene that is over-expressed compared to an unmodified algae, wherein synthesis of starch by the modified algae is increased relative to the unmodified algae; isolating the modified algae from the growth medium; and processing the algae to produce a starch. Also disclosed herein are methods of producing starch from a modified algae comprising: growing a modified algae in a growth medium, wherein the modified algae comprises a mutated isoamylase gene; and one or more copies of an un-mutated isoamylase expression construct; wherein synthesis of starch by the modified algae is increased relative to the unmodified algae; isolating the algae from a growth medium; and processing the algae to produce a starch.

Disclosed herein are modified algae having a mutated isoamylase gene and one or more copies of an unmutated isoamylase expression construct, wherein the algae accumulate greater amounts of starch than unmodified algae. In some cases, the mutated isoamylase gene is a disrupted gene. In some cases the un-mutated isoamylase expression construct comprises the genomic isoamylase coding sequence. In some cases the algae is *C. reinhardtii*. In some cases, the algae may be complemented sta7 mutants of *C. reinhardtii*.

Wild-type and modified algae are disclosed. In some cases the algae is any algae comprising an isoamylase gene, or any algae that can produce starch. In other embodiments, the alga can be red or green algae. In many embodiments the alga is chosen from the genera *Scenedesmus, Prototheca, Chlorella, Chlamydomonas, Botryococcus, Haematococcus, Dunaliella, Isochrysis, Tetraselmis*. In some cases the alga is a green alga (Chlorophyceae), red alga (Rhodophyceae), or Dinophyta (dinoflagellates) or Glaucophyta. In some cases, the alga is from the division of chlorophyta. In various cases the algae may be *Chlamydomonas reinhardtii, Chlamydomonas sp, Chlamydomonas actinochloris, Chlamydomonas agregata, Chlamydomonas augustae, Chlamydomonas cf debaryana, Chlamydomonas cf peterfii, Chlamydomonas cf typica, Chlamydomonas chlorococcoides, Chlamydomonas dorsoventralis, Chlamydomonas geitleri, Chlamydomonas macropyrenoidosa, Chlamydomonas moewusii, Chlamydomonas nivalis, Chlamydomonas peterfii, Chlamydomonas segnis, Chlamydomonas subtilis, Chlorella pyrenoidosa, Chlorella variabilis, Chlorella anitrata, Chlorella antarctica, Chlorella aureoviridis, Chlorella candida, Chlorella capsulata, Chlorella desiccata, Chlorella ellipsoidea, Chlorella emersonii, Chlorella usca, Chlorella usca var vacuolata, Chlorella glucotropha, Chlorella infusionum, Chlorella infusionum* var *Actophila, Chlorella infusionum* var *Auxenophila, Chlorella kessleri, Chlorella luteoviridis, Chlorella luteoviridis* var *aureoviridis, Chlorella luteoviridis* var *Lutescens, Chlorella miniata, Chlorella minutissima, Chlorella mutabilis, Chlorella nocturna, Chlorella parva, Chlorella photophila, Chlorella pringsheimii, Chlorella protothecoides, Chlorella regularis, Chlorella regularis* var *minima, Chlorella regularis* var *umbricata, Chlorella reisiglii, Chlorella saccharophila, Chlorella saccharophila* var *ellipsoidea, Chlorella salina, Chlorella simplex, Chlorella sorokiniana, Chlorella sp, Chlorella sphaerica, Chlorella stigmatophora, Chlorella vanniellii, Chlorella vulgaris, Chlorella vulgaris tertia, Chlorella vulgaris* var *airidis, Chlorella vulgaris* var *vulgaris, Chlorella vulgaris* var *vulgaris tertia, Chlorella vulgaris* var *vulgaris viridis, Chlorella xanthella, Chlorella zofingiensis, Prototheca moriformis, Prototheca sp, Prototheca stagnora, Prototheca zopfii, Scenedesmus obliquus, Scenedesmus quadricauda, Scenedesmus maximus, Scenedesmus opoliensis, Scenedesmus aramalus, Scenedesmus dimorphus, Scenedesmus sp, Dunaliella salina, Dunaliella tertiolecta, Dunaliella sp,* or *Cyanidioschyzon merolae*.

As used herein, wild-type algae lack mutations in the starch biosynthetic pathway, but may comprise mutant sequences in other pathways that can aid in growth of alga in a laboratory setting or a commercial setting. In some cases, the disclosed wild-type algae is any algae comprising an isoamylase gene, or any algae that can produce starch. In other embodiments, the wild-type alga can be red or green algae. In many embodiments the wild-type alga is chosen from the genera *Scenedesmus, Prototheca, Chlorella, Chlamydomonas, Botryococcus, Haematococcus, Dunaliella, Isochrysis, Tetraselmis*. In some cases the wild-type alga is a green alga (Chlorophyceae), red alga (Rhodophyceae), or any alga from the division of *chlorophyta*. In some cases, the wild-type alga is CC-124, or D66. In some cases the wild-type algae may be selected from a group consisting of CC-1009, CC-1010, CC-1092, CC-1093, CC-124, CC-124 J, CC-125, CC-1373, CC-1480, CC-1481, CC-1690, CC-1691, CC-1692, CC1952, CC2342, CC-2399, CC-2482, CC-2494, CC-277, CC-2931, CC425, CC-4425, CC-620, CC-621, CCAP 11/32A, CCAP 11/32B, CCAP 11/32D, CCAP11/132, CF-1, CF-2, CW15, D66, D67, NIVA Chl13, NIVA Chl21, SAG 11-31, SAG 11-32a, SAG 11-32b, SAG 11-32c, SAG 18.79, SAG 23.90, SAG 54.72, SAG 7.73, SAG 73.72, SAG 77.81, SAG 81.72, SAG 83.81, UTEX 1062, UTEX 2243, UTEX 2244, UTEX 2246, UTEX 2247, UTEX 2337, UTEX 89, UTEX 90.

In many cases, the disclosed modified algae over-expresses isoamylase. In some embodiments, over-expression of isoamylase is due to the presence of additional copies of the isoamylase coding sequence, for example by transformation of an alga with an isoamylase expression construct. In some cases, isoamylase expression constructs may comprise a genomic isoamylase coding sequence. In some cases, over-expression may be due to modification of the control sequences of the genomic isoamylase gene, for example mutation of the isoamylase promoter sequence, or replacement of the isoamylase promoter sequence with a more active promoter sequence. In many cases, the isoamylase expression construct may be integrated into the algae genome, in other cases the isoamylase expression construct may be an extra-chromosomal sequence, such as a plasmid. Such methods are well known to one of skill in the art and can be found in Lumbreras, V., D. R. Stevens, and S. Purton, 1998, Efficient foreign gene expression in *Chlamydomonas reinhardtii* mediated by an endogenous intron. Plant J. 14:441-447; The *Chlamydomonas* Sourcebook, Second Edition, Academic Press, Oxford; Harris, E. H. (Ed.) 2009; and The *Chlamydomonas* Sourcebook: a comprehensive guide to biology and laboratory use. Academic Press, San Diego In E. Harris (ed.), 1989, which are expressly incorporated by reference herein.

Over-expression of the isoamylase gene may be relative to a wild-type, parent, or unmodified algae. In many cases the expression of the isoamylase gene as mRNA in the modified algae is higher than the expression of the isoamylase gene in the wild-type, parent, or unmodified algae. Isoamylase gene expression may be quantified by various methods known in the art. For example, levels of mRNA can be measured by northern blotting which can provide size and sequence information about the mRNA molecules. In northern blot analysis of isoamylase expression, a sample of RNA from modified or unmodified algae is separated on an agarose gel and hybridized to a labeled RNA sequence of isoamylase. The labeled isoamylase RNA is then detected and in many cases quantitated. Reverse transcription quantitative polymerase chain reaction (RT-PCR followed with qPCR) can also be used to quantitate gene expression levels. RT-PCR first generates a DNA template from the mRNA by reverse transcription, which is called cDNA. This cDNA template is then used for qPCR where the change in fluorescence of a probe changes as the DNA amplification process progresses. qPCR can provide information on the number of copies of mRNA per cell and/or the relative amounts of mRNA in two different cells or cell-line. Tagging single mRNA molecules with fluorescent barcodes (nanostrings) can also be used. In this technique, fluorescence of a single mRNA molecule can be detected. Microarrays can also be used to measure mRNA levels.

In some embodiments, modified algae can have a mutated genomic isoamylase gene. In some embodiments, algae with a mutated genomic isoamylase gene can be referred to as a starch mutant or a "starchless" mutant. The disclosed starch mutants can include various phenotypic changes in starch content and starch structure. In some embodiments, two *Chlamydomonas reinhardtii* starch mutants, sta6 and sta7, are disclosed. sta6 and sta7 are single gene disruptions that result in a "starchless" phenotype. In many cases, the starchless mutant cell is compared with a wild-type cell, for example the sta7 mutant may be compared with CC124, or some other *C. reinhardtii* strain that lacks mutations in starch biosynthesis.

A starchless phenotype can have lower levels of starch granule accumulation, for example, less than about 30% of wild-type (unmodified) starch accumulation. In some cases, starchless mutants accumulate less than about 25%, 20%, 15%, 10%, 9%, 8%, 7%, 6%, 5%, 4%, 3%, 2%, or 1%, and/or greater than about 0%, 1%, 2%, 3%, 4%, 5%, 6%, 7%, 8%, 9%, 10%, 15%, 20%, or 25% of wild-type starch accumulation. Starch assays are well known in the art, and exemplary assays are described in Example 2, below. Starchless phenotypes can result from various genetic modifications, include gene disruption, gene mutation, gene knock-out, coding sequence mutation, control region mutation, etc. Such methods are well known to one of skill in the art and can be found in Lumbreras, V., D. R. Stevens, and S. Purton, 1998, Efficient foreign gene expression in *Chlamydomonas reinhardtii* mediated by an endogenous intron. Plant J. 14:441-447; The *Chlamydomonas* Sourcebook, Second Edition, Academic Press, Oxford; Harris, E. H. (Ed.) 2009; and The *Chlamydomonas* Sourcebook: a comprehensive guide to biology and laboratory use. Academic Press, San Diego In E. Harris (ed.), 1989, which are expressly incorporated by reference herein. Genetic mutations include nucleic acid sequence re-arrangements, deletions, insertions, and substitutions.

In some embodiments, the disrupted locus of a starchless mutant can code for an enzyme. In some cases, the disrupted locus can allow expression of an enzyme, or the disrupted locus can code for a mutant enzyme. In embodiments where enzyme expression can occur, expression of the enzyme coding sequence may be lower than in the wild-type cell. In some cases, the starchless mutant may express lower levels of a starch biosynthetic gene transcript than the wild-type cell, for example less than about 100%, 90%, 80%, 70%, 60%, 50%, 40%, 30%, 20%, 10%, or 5% of the wild-type expression level.

In many embodiments, different starchless mutants are described that may have distinct disruptions and/or distinct phenotypes. In some cases, the starchless mutant comprises a disrupted gene involved in carbohydrate biosynthesis, for example the starchless mutants sta6 and sta7. sta6 and sta7 comprise unique disrupted loci resulting in unique phenotypes. In sta6, the small, catalytic subunit of ADP-glucose pyrophosphorylase (AGPase-SS) is disrupted, and this mutant can accumulate less than 1% of the starch observed in wild-type cells under conditions of nitrogen deprivation. The sta7 mutant contains a disrupted isoamylase gene as described in Posewitz, M. C., S. L. Smolinski, S. Kanakagiri, A. Melis, M. Seibert, and M. L. Ghirardi. 2004. Hydrogen photoproduction is attenuated by disruption of an isoamylase gene in *Chlamydomonas reinhardtii*. Plant Cell 16:2151-2163, which is expressly incorporated herein by reference.

In many cases, a starchless mutant has lowered levels of starch, but can accumulate a soluble glycogen-like product. In some cases, depending on the culturing conditions, sta7 can contain approximately 10% of the glucose equivalents found in starch in control strains. In various embodiments, starchless mutants can comprise disruptions in various loci. In some various different disruptions can be made at the same locus. In most cases, a disrupted locus results in lowered expression of a starch biosynthetic gene, or expression of a mutated gene with lowered activity. Where the starch biosynthetic gene codes for an enzyme, the mutated enzyme may be less active than the wild-type enzyme.

In most cases, the modified algae over-expresses isoamylase in a wild-type background. In other cases, the modified algae can have a mutated isoamylase gene. In some cases the mutated gene is a disrupted isoamylase gene, in other cases the gene sequence can be modified by insertions, deletions, substitutions, or rearrangements in the nucleic acid sequence of the isoamylase gene. In some embodiments, the isoamylase gene comprises coding and non-coding sequences, for example untranslated and/or intervening sequences such as introns. A mutated gene can result in no expression, reduced expression, or increased expression of the mutated isoamylase gene.

Isoamylase-Complemented Algae

In many embodiments, the disclosed modified algae can over-express isoamylase. In some embodiments, the modified algae is a modified wild-type cell comprising additional copies of an isoamylase gene. In other embodiment, the modified algae is a wild-type algae with a genomic copy of isoamylase that is modified to over-express isoamylase. In various embodiments, the disclosed modified algae comprises one or more copies of an isoamylase expression cassette or isoamylase expression construct. In many embodiments, modified algae comprising one or more copies of an isoamylase expression cassette or isoamylase expression construct over-express isoamylase. In various embodiments, a modified starchless mutant is disclosed. In some embodiments, the modified starchless mutant includes an isoamylase expression construct or expression cassette.

Disclosed isoamylase expression cassettes/constructs can include control regions and an isoamylase coding region. In some embodiments, the control regions and coding regions are from the isoamylase locus of the algae. For example, in cases where the modified algae is a sta7 mutant of *C. reinhardtii*, the expression construct may comprise the genomic isoamylase locus of *C. reinhardtii*. In some embodiments the isoamylase expression cassette or expression construct comprises the genomic sequence of *C. reinhardtii* isoamylase as in SEQ ID NO:3. In some cases, the isoamylase expression cassette or expression construct comprises a selectable marker for example, a phleomycin resistance gene. In some cases, the isoamylase expression cassette or expression construct may include plasmid backbone sequence, for example from pUC19. The use of a bacterial plasmid backbone may aid in manipulation, construction, and production of the isoamylase expression construct. In other embodiments, the isoamylase expression construct may comprise an isoamylase cDNA and control sequences from other than an algal isoamylase gene. In many cases, the isoamylase expression construct or expression cassette produces a mRNA that codes for a protein with homology to SEQ ID NO:1 and/or has isoamylase enzyme activity.

In some embodiments, the expression construct may comprise an isoamylase coding region from an alga other than the modified alga, or from a non-alga organism. In some cases, the expression construct may comprise genomic isoamylase coding sequences.

Isoamylase expression constructs/cassettes may reside on plasmids, or other extrachromosomal nucleic acids, or the constructs may be integrated into the genome of the modified algae. In some cases, the construct or cassette is integrated into a nuclear genome of the genome of a mitochondria or plastid.

Isoamylase coding regions can be derived from various sources. In some cases, isoamylase coding regions can code for an algal isoamylase, an isoamylase homologous to an algal isoamylase, or a non-algal isoamylase. In most embodiments, the isoamylase coding region codes for a polypeptide with isoamylase enzymatic activity.

Isoamylase is a carbohydrate de-branching enzyme. In most embodiments the disclosed isoamylase comprises an enzyme that catalyzes the hydrolysis of 1,6-α-glycosidic branch linkages in glycogen and amylopectin. In many cases isoamylase has an EC number of 3.2.1.68.

In various embodiments, the isoamylase enzyme activity coded for by the expression construct may be equivalent to the isoamylase enzyme of an unmodified algae. In other cases, the enzyme activity of the enzyme coded for by the isoamylase expression construct is greater than the enzyme activity of the isoamylase enzyme coded for by the unmodified algae. In some cases, the modified algae expresses more isoamylase enzyme than an unmodified strain.

In some cases, the disclosed isoamylase gene sequences can be homologous or identical to SEQ ID NOs:2 or 3 or portions thereof, for example more than about 5 nt, 10 nt, 15 nt, 20 nt, 25 nt, 30 nt, 35 nt, 40 nt, 45 nt, 50 nt, 60 nt, 70 nt, 80 nt, 90 nt, 100 nt, 150 nt, 200 nt, 300 nt, 400 nt, 500 nt, or 600 nt, 700 nt, 800 nt, 900 nt, 1.0 k nt, 1.1 k nt, 1.2, nt, 1.3 k nt, 1.4 k nt, 1.5 k nt, 1.6 k nt, 1.7 k nt, 1.8 k nt, 1.9 k nt, 2.0 k nt, 2.5 k nt, 3.0 k nt, 4.5 k nt, 5.5 k nt, 5.5 k nt, 6.0 k nt, 6.5 k nt, 7.0 k nt, 7.5 k nt, 8.0 k nt, 8.5 k nt, 9.0 k nt, 9.5 k nt, 10.0 k nt, 10.5 k nt, 11.0 k nt, 11.5 k nt, 12.0 k nt, 12.5 k nt, and/or less than about 13.0 k nt, 12.5 k nt, 12.0 k nt, 11.5 k nt, 11.0 k nt, 10.5 k nt, 10.0 k nt, 9.5 k nt, 9.0 k nt, 8.5 k nt, 8.0 k nt, 7.5 k nt, 6.0 k nt, 5.5 k nt, 5.0 k nt, 4.5 k nt, 4.0 k nt, 3.5 k nt, 3.0 k nt, 2.5 k nt, 2.0 k nt, 1.9 k nt, 1.8 k nt, 1.7 k nt, 1.6 k nt, 1.5 k nt, 1.4 k nt, 1.3 k nt, 1.2 k nt, 1.1 k nt, 1.0 k nt, 900 nt, 800 nt, 700 nt, 600 nt, 500 nt, 400 nt, 300 nt, 200 nt, 150 nt, 90 nt, 80 nt, 70 nt, 60 nt, 55 nt, 50 nt, 45 nt, 40 nt, 35 nt, 30 nt, 25 nt, 20 nt, 15 nt, 10 nt, or 5 nt. In various cases, the homologous sequences can include deleted nucleotides or inserted nucleotides.

In various cases the homologous nucleotide sequences can be aligned by a nucleotide sequence alignment algorithm. For example, blastn for aligning two nucleotide sequences, wherein the program is optimized for highly similar sequences (megablast) or for somewhat similar sequences (blastn; this can be useful where sequences have less than about 90% identity or the sequences have low complexity). In various cases the maximum target sequence is set to the length of the longer of the two sequences to be aligned, the expected threshold can be 10, the word size can be 28, the match/mismatch scores can be −1, −2 and the gap costs linear. In various cases of homology between nucleotide sequences, homology can be expressed as percent identity.

In some variations the nucleotide sequences, when aligned with the sequences of SEQ ID NO:2, can have identity of more than about 40%, 45%, 50%, 55%, 60%, 65%, 70%, 75%, 80%, 85%, 90%, or 95% and/or less than about 100%, 95%, 90%, 85%, 80%, 75%, 70%, 65%, 60%, 55%, 50%, or 45% identities. In various cases the sequence alignment can have gaps of less than about 15%, 14%, 13%, 12%, 11%, 10%, 9%, 8%, 7%, 6%, 5%, 4%, 3%, 2%, 1%.

Modified Algae

Modified algae are described. In various cases the described mutations can be made in, and nucleic acid sequences can be introduced into various organisms to create modified algae. In various embodiments, modified biosynthetic pathway may be introduced into the organism In some cases, mutants in starch biosynthetic pathways are extant in various organisms. In some cases, mutations may be made in an organism by insertional mutagenesis and/or homologous recombination. In most cases integration into the genome may be random. In some cases, mutant organisms may be selected by the use of a selectable marker. In some cases, nuclear, chloroplast, or plastid genes may be mutated. Nucleic acid sequences may be introduced into an organism in a variety of ways, for example chemical transformation, electroporation, and/or with glass beads, as described in K. Kindle, High-frequency nuclear transformation of *Chlamydomonas reinhardtii*, PNAS, Vol 87, pp. 1288-1232 (1990), which is expressly incorporated by reference herein. This process may be referred to as transformation. In various cases, the nucleic acid sequences introduced into the organism can include promoters, un-translated sequences, coding sequences, or combinations thereof. In many cases these sequences can be operably linked, for example on an expression cassette, insertional cassette with a selectable marker.

In various cases, the nucleic acid sequences can be incorporated into the genome of the modified algae, or are included on a plasmid or vector in the modified algae. In some cases, nucleic acid sequences can be translocated, re-arranged, deleted, or duplicated within the modified algae. Nucleic acid sequences that are translocated, re-arranged, deleted, or duplicated include single derivatised nucleotides, native nucleotides, single nucleotides, and multiple nucleotides. In various cases, the disclosed modified algae can further comprise native or non-native nucleic acid sequences.

Stably integrated nucleic acid sequences can be passed to progeny. In various cases, stably integrated nucleic acids can have selectable markers that can aid in selecting modified algae. In various cases, selectable markers must be retained by the progeny. In various cases, a selectable marker can confer resistance to a drug or chemical, which can retard the growth of organisms which lack the resistance selectable marker. In various cases, the selectable marker can be an antibiotic resistance gene.

Homology Based on Hybridization

In some cases, the inventive nucleotide sequences can hybridize to the sequences of SEQ ID NOs:2 or 3. Hybridization can occur under various stringency conditions. Stringency refers to the binding of two single stranded nucleic acids via complementary base pairing. Extensive guides to the hybridization of nucleic acids can be found in: Tijssen, Laboratory Techniques in Biochemistry and Molecular Biology-Hybridization with Nucleic Acid Probes Part I, Ch. 2, "Overview of principles of hybridization and the strategy of nucleic acid probe assays" (1993), Elsevier, N.Y.; and Sambrook et al., Molecular Cloning: A Laboratory Manual (3rd ed.) Vol. 1-3 (2001), Cold Spring Harbor Laboratory, Cold Spring Harbor Press, N.Y. The phrases "hybridizing specifically to", "specific hybridization", and "selectively hybridize to", refer to the preferential binding, duplexing, or hybridizing of a nucleic acid molecule to a particular probe under stringent conditions. The term "stringent conditions" refers to hybridization conditions under which a probe will hybridize preferentially to its target subsequence, and to a lesser extent, or not at all, to other sequences in a mixed population (e.g., a DNA preparation from a tissue biopsy). "Stringent hybridization" and "stringent hybridization wash conditions" are sequence-dependent and are different under different environmental parameters.

Generally, highly stringent hybridization and wash conditions are selected to be about 5° C. lower than the thermal melting point (Tm) for a specific sequence at a defined ionic strength and pH. The Tm is the temperature at which 50% of the target sequence hybridizes to a perfectly matched probe. Very stringent conditions are selected to be equal to the Tm for a particular probe. Often, a high stringency wash is preceded by a low stringency wash to remove background probe signal. An example of stringent hybridization conditions for hybridization of complementary nucleic acids which have more than 100 complementary residues on an array is 42° C. using standard hybridization solutions, with the hybridization being carried out overnight. An example of highly stringent wash conditions is a 0.15 M NaCl wash at 72° C. for 15 minutes. An example of stringent wash conditions is a wash in 0.2× Standard Saline Citrate (SSC) buffer at 65° C. for 15 minutes. An example of a medium stringency wash for a duplex of, for example, more than 100 nucleotides, is 1×SSC at 45° C. for 15 minutes. An example of a low stringency wash for a duplex of, for example, more than 100 nucleotides, is 4× to 6×SSC at 40° C. for 15 minutes.

In some cases, the disclosed gene nucleic acid sequences can bind to *C. reinhardtii* isoamylase gene sequences with low stringency.

Form of Nucleotide Sequences

In various cases the homologous nucleotide sequences can be single-stranded, double stranded, or a combination thereof. In some variations, the nucleotide sequences can comprise natural nucleic acids, synthetic nucleic acids, non-natural nucleic acids, and/or nucleic acid analogs. The nucleotide sequences can further comprise other non-nucleic acid molecules such as amino acids, and other monomers.

In various cases, the nucleic acids of the disclosed nucleotide sequences can include nucleotides that are metabolized in a manner similar to naturally occurring nucleotides. Also included are nucleic-acid-like structures with synthetic backbone analogues including, without limitation, phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs) (see, e.g.: "Oligonucleotides and Analogues, a Practical Approach," edited by F. Eckstein, IRL Press at Oxford University Press (1991); "Antisense Strategies," Annals of the New York Academy of Sciences, Volume 600, Eds. Baserga and Denhardt (NYAS 1992); Milligan (1993) J. Med. Chem. 36:1923-1937; and "Antisense Research and Applications" (1993, CRC Press)). PNAs contain non-ionic backbones, such as N-(2-aminoethyl) glycine units. Phosphorothioate linkages are described in: WO 97/03211; WO 96/39154; and Mata (1997) Toxicol. Appl. Pharmacol. 144:189-197. Other synthetic backbones encompassed by this term include methyl-phosphonate linkages or alternating methyl-phosphonate and phosphodiester linkages (Strauss-Soukup (1997) Biochemistry 36: 8692-8698), and benzyl-phosphonate linkages (Samstag (1996) Antisense Nucleic Acid Drug Dev 6: 153-156).

Expression Control Sequences

In various cases the disclosed gene nucleotide sequences can comprise control sequences having transcriptional regulatory activity. Control sequences with transcriptional regulatory activity can include sequences that can affect transcription or expression of a nearby or distal transcribed sequences. In various cases, the disclosed control sequences can enhance or suppress transcription from nearby or distal genes and coding sequences. In various cases, specific sequences can be used to enhance and/or suppress transcription from a nearby gene. In various cases, these nucleic acid sequences can provide binding or recognition sequences for proteins and enzymes involved in transcription, for example TATA binding protein, RNA polymerase (I, II, or III) and DNA binding proteins, such as transcription factors. Disclosed nucleotide sequences can comprise core promoter sites, transcription initiation sites, proximal promoter sites, or distal promoter sites.

In various cases, control activity of a nucleotide sequence can be tested by the use of a coding sequence operatively connected to the nucleotide sequence. In various cases the coding sequence can be a reporter gene. In various cases the reporter can be screenable or selectable. Selectable reporters can be required for survival in certain media, for example in the presence of an antibiotic. Screenable reporters can be observed visually, or easily assayed.

In various cases, less than the entire control region can be used to regulate transcriptional expression of a nearby gene. In various cases portions of the disclosed control regions ranging from less than about 700 nt (nucleotides), 600 nt, 500 nt, 400 nt, 300 nt, 200 nt, 100 nt, 90 nt, 80 nt, 70 nt, 60 nt, 50 nt or 40 nt, and/or in various cases more than about 50 nt, 60 nt, 70 nt, 80 nt, 90 nt, 100 nt, 200 nt, 300 nt, 400 nt, 500 nt, or 600 nt can aid in regulating gene expression. In various cases the described control sequence can be a contiguous sequence. In other cases non-contiguous portions of a control sequence can be connected, and internal portions removed. In various cases portions of a control sequence can be inverted relative to their native orientation. In various cases the control sequences can have internal nucleotides removed. In other cases, nucleotides can be added, or deleted, or the identity of a nucleotide changed.

The disclosed control regions can comprise nucleotide sequence from more than one control region. In various cases the multiple control regions can be operably linked. In various cases the operably linked control regions can be in the same orientation, for example a direct repeat. In other cases, the control regions can be oriented in opposite directions.

The disclosed expression control sequences can comprise control regions can be used with promoters, enhancers, and other genetic regulatory elements from different control regions.

In various cases, portions of the expression control sequences can have transcriptional promoter activity. In these cases, the control regions can initiate transcription of an operably linked nucleic acid sequence, in various cases the linked nucleic acid is a coding sequence, gene, or non-coding sequence. In some variations, transcription can initiate within the control sequence, in other cases, transcription initiates at an operably linked nucleic acid sequence. In various cases, the coding sequence can code for an N-terminal methionine of an operably linked coding sequence.

Isoamylase Expression Constructs/Cassettes

In various cases, the disclosed isoamylase gene nucleotide sequences can be operably linked to a control sequence. Operable linking of nucleic acid sequences can include where a nucleic acid is placed into a functional relationship with another nucleic acid sequence. In various cases operably linking two or more nucleic acid sequences can form an expression construct or cassette. An expression construct or expression cassette can comprise one or more coding sequences and control sequences that regulate expression of the coding sequence. In various cases, the control sequence can be a promoter sequence, and the coding sequence can comprise untranslated sequence or region that can further comprise a polyadenylation site. In various cases, the expression cassette can be contained on a plasmid or vector. In various cases, expression cassettes further comprise nucleic acid sequences allow for selection or retention of the cassette within the organism. In various cases, an expression construct can include transcriptional and translational regulatory nucleic acid sequences and nucleic acid sequences encoding a polypeptide. In some variations, the transcriptional and translational regulatory sequences can include promoter sequences, ribosomal binding sites, transcriptional start and stop sequences, translational start and stop sequences, and enhancer or activator sequences.

In various cases, the expression constructs can be incorporated into a genome of a cell, or can be an unincorporated plasmid or vector. In various cases, a plasmid or vector introduced into a cell can later become incorporated into the cell's genome. In various cases, genome can refer to nucleic acids including coding, non-coding, and regulatory sequences in linear or circular form. In various cases a genome can be one or several chromosomes. In various cases a genome can reside in the cytoplasm, nucleus, or organelles such as mitochondria, plastids, and chloroplasts.

In some cases, the disclosed isoamylase gene sequences can be operably linked to heterologous control regions. In some cases control regions operatively linked to an isoamylase coding region can result in more or less expression of isoamylase than the native isoamylase control sequence. In some cases, the control/promoter region can result in the isoamylase gene being expressed in response to specific stimuli.

Disclosed herein are polypeptides with isoamylase activity. In some cases, the polypeptides may be or have homology to isoamylase from *Chlamydomonas reinhardtii*. The amino acid sequence of *Chlamydomonas reinhardtii* isoamylase is at SEQ ID NO:1. An isoamylase enzyme, as used herein, has an activity defined as EC 3.2.1.68.

Polypeptides disclosed herein can include amino acid sequences that are identical to the amino acid sequence of *Chlamydomonas reinhardtii* isoamylase. In other cases, the claimed isoamylase polypeptides include amino acid sequences that can comprise conservative amino acid substitutions as compared to the disclosed *Chlamydomonas reinhardtii* isoamylase sequence. Conservative amino acid substitutions can include amino acids that share characteristics with the substituted amino acid. In various cases, substitution can be made without significant change in the structure or function of the polypeptide.

Conservative amino acid substitutions can be made on the basis of relative similarity of side-chain size, charge, hydrophobicity, hydrophilicity, etc. In various cases, substitutions can be assayed for their effect on the function of the protein by routine testing. Conserved amino acid substitutions include amino acids with similar hydrophilicity value, as wherein amino acids have a hydropathic index which can be based upon an amino acid's hydrophobicity and charge. In various cases, conserved amino acid substitutions can be made between amino acids of the same class, for example non-polar amino acids, acidic amino acids, basic amino acids, and neutral amino acids. Conservative substitutions can also be based upon size or volume. Amino acids can also be classified based upon their ability to form or break a given structure, such as an alpha helix, beta sheet, or intra- or inter-molecular interaction. In various cases conservative amino acid substitutions are based upon more than one characteristic.

Currently disclosed polypeptides can include both natural and non-natural amino acids. In various cases, natural amino acid side chains can be substituted with non-natural side chains. In various cases, amino acids can be derivatised.

The disclosed polypeptides include polypeptides that are homologous to the sequence of *Chlamydomonas reinhardtii* isoamylase. Homology can be expressed as % identity or % similar or % positive. In various cases, % identity is a percentage of amino acids that are identical between two aligned polypeptides, and % similar or % positive is a percentage of amino acids that are non-identical but represent conservative substitutions; for example, lysine to arginine can be considered a conservative substitution where charge is considered.

In various cases, two polypeptides can be aligned by algorithms, for example BLASTp. In various cases, the BLASTp perameters can be set with a maximum target sequence length equal to, greater, or less than the length of the longer of the two polypeptides, the expect threshold can be set to 10, the word size to 3, and scoring matrix can be BLOSUM62, with gap costs of 11 for existence and 1 for extension. BLASTp can report homology of aligned polypeptides as "Identities" and "Positives." The aligned sequences can include gaps to achieve the alignment.

In various cases, homology of amino acid sequences can reflect the percentage of identity or positives when optimally aligned as described above. In various cases, the % homology (% positive) or % identity can be calculated by dividing the number of aligned amino acids within a comparison window. A comparison window can be the entire length of one or the other polypeptides, if the two polypeptides are of unequal length. In other cases, the comparison window can be a portion of one of the polypeptides. In various cases the comparison window for measuring homology or identity of two polypeptide sequences is greater than about 40 aa (amino acids), 45 aa, 50 aa, 55 aa, 60 aa, 65 aa, 70 aa, 75 aa, 80 aa, 85 aa, 90 aa, 95 aa, 100 aa, 150 aa, or 200 aa, and/or less than about 200 aa, 150 aa, 100 aa, 95 aa, 90 aa, 85 aa, 80 aa, 75 aa, 70 aa, 65 aa, 60 aa, 55 aa, 50 aa, or 45 aa.

In various cases, the claimed amino acid sequences can have % identity or % homology (% positive) over a given comparison window, that is greater than about 60%, 65%, 70%, 75%, 80%, 85%, 90%, 91%, 92%, 93%, 94%, 95%, 96%, 97%, 98%, or 99% and/or less than about 100%, 99%, 98%, 97%, 96%, 95%, 94%, 93%, 92%, 91%, 90%, 85%, 80%, 75%, or 70%.

In various cases, a sequence alignment can be performed using various algorithms, including dynamic, local, and global alignment. For example, the algorithm of Smith and Waterman, 1981, Adv. Appl. Math 2: 482; the alignment algorithm of Needleman and Wunsch, 1970, J. Mol. Biol. 48:443; the similarity method of Pearson and Lipman, 1988, Proc. Natl. Acad. Sci. USA 85: 2444. In various cases, computer programs can implement these algorithms (such as EMBOSS, GAP, BESTFIT, FASTA, TFASTA BLAST, BLOSUM, etc.).

In alternative cases, conserved amino acid substitutions can be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In some cases, conserved amino acid substitutions can be made where an amino acid residue is substituted for another having a similar hydrophilicity value (e.g., within a value of plus or minus 2.0), where the following can be an amino acid having a hydropathic index of about −1.6 such as Tyr (−1.3) or Pro (−1.6)s are assigned to amino acid residues: Arg (+3; 0); Lys (+3.0); Asp (+3.0); Glu (+3.0); Ser (+0.3); Asn (+0.2); Gln (+0.2); Gly (O); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative cases, conserved amino acid substitutions can be made where an amino acid residue is substituted for another having a similar hydropathic index (e.g., within a value of plus or minus 2.0). In such cases, each amino acid residue can be assigned a hydropathic index on the basis of its hydrophobicity and charge characteristics, as follows: Iie (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative cases, conserved amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (J. Mol. Bio. 179:125-142, 184). Genetically encoded hydrophobic amino acids include Gly, Ala, Phe, Val, Leu, Iie, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which can contain one or more substituents such as —OH, —SH, —CN, —F, —Cl, —Br, —I, —NO2, —NO, —NH2, —NHR, —NRR, —C(O)R, —C(O)OH, —C(O)OR, —C(O)NH2, —C(O)NHR, —C(O)NRR, etc., where R is independently (C1-C6) alkyl, substituted (C1-C6) alkyl, (C0-C6) alkenyl, substituted (C1-C6) alkenyl, (C1-C6) alkynyl, substituted (C0-C6) alkynyl, (C5-C20) aryl, substituted (C0-C20) aryl, (C6-C26) alkaryl, substituted (C6-C26) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Tryp.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

A % amino acid sequence identity value is determined by the number of matching identical residues divided by the total number of residues of the "longer" sequence in the comparison window. The "longer" sequence is the one having the most actual residues in the comparison window (gaps introduced by WU-Blast-2 to maximize the alignment score are ignored).

The alignment can include the introduction of gaps in the sequences to be aligned. In addition, for sequences which contain either more or fewer amino acids than the protein encoded by the sequence the disclosed polypeptide, it is understood that in one case, the percentage of sequence identity will be determined based on the number of identical amino acids in relation to the total number of amino acids. In percent identity calculations relative weight is not assigned to various manifestations of sequence variation, such as, insertions, deletions, substitutions, etc.

In one case, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Coding Sequences

In various cases, nucleotide sequences encoding the isoamylase polypeptide sequences of SEQ ID NOS:1 are included. These nucleotide coding sequences can be translated into a polypeptide having an amino acid sequence identical to the disclosed polypeptide sequence. The inventive coding sequences can further comprise untranslated sequences, for example poly-adenylation sequences. The inventive coding sequences can also comprise intron or intervening, non-translated, sequence that are spliced out of a transcribed mRNA prior to translation. In various cases the transcribed mRNA can be capped with a terminal 7-methylguanosine.

In some variations, due to the degeneracy of the genetic code, multiple nucleotide coding sequences can encode the same polypeptide sequence. These inventive nucleic acid coding sequences can also be homologous to nucleotide sequences that encode the disclosed polypeptides. The nucleotide coding sequences can be aligned by BLASTn, as described above. In various cases the homology (or identities in BLASTn) of these aligned nucleotide sequences can be greater than about 40%, 45%, 50%, 55%, 60%, 65%, 70%, 75%, 80%, 85%, 90%, or 95% and/or less than about 100%, 95%, 90%, 85%, 80%, 75%, 70%, 65%, 60%, 55%, 50%, or 45%. In various cases, the homologous aligned sequences can be less than about 700 nt, 600 nt, 500 nt, 400 nt, 300 nt, 200 nt, 100 nt, 90 nt, 80 nt, 70 nt, 60 nt, 50 nt or 40 nt, and/or more than about 50 nt, 60 nt, 70 nt, 80 nt, 90 nt, 100 nt, 200 nt, 300 nt, 400 nt, 500 nt, or 600 nt.

In various cases, the coding sequence directs transcription of a ribonucleic acid sequence that can be translated into amino acid sequence according to the standard genetic code. In various cases, the code can include variations to the canonical code. In some variations, the coding sequence can include introns, or intervening sequences that do not code for amino acids, but can be transcribed and later removed before the ribonucleic acid is translated into a polypeptide.

Sequences Related to Lipid and Starch Biosynthesis.

The disclosed organisms, nucleic acid sequences, amino acid sequences, and methods can be used to increase lipid or starch biosynthesis. In various cases, lipid biosynthesis can include lipid metabolism, such as synthesis of fatty acids, assembly of triacylglycerides, and activation of lipids. In various cases the disclosed nucleic acid sequences and amino acid sequences are related to lipid metabolic pathway genes, fatty acids biosynthetic genes, triacylglycerides assembly genes, lipid activation genes, and genes that can regulate transcription and translation of these genes, as well as proteins that regulate these genes and proteins that regulate the enzymes in these pathways.

In various cases, starch biosynthesis can include starch metabolism, such as the synthesis of carbohydrates, and assembly, branching, de-branching, and modification of polysaccharides. In various cases the disclosed organisms, nucleic acid sequences, and amino acid sequences are related to starch metabolic pathway genes, proteins, and enzymes, and genes and proteins that can regulate transcription and translation of these genes, as well as proteins that regulate these genes and proteins that regulate the enzymes in these pathways.

In some embodiments, starch biosynthetic genes include isoamylase, the large and small subunits of ADP-glucose pyrophosphoryase, starch synthase, branching, and de-branching enzymes, for example isoamylase.

Growth of Inventive Organisms

In some cases, for example where the organism is a plant, the inventive organism may be grown in various environments, for example in soil. In various cases, the described organisms can be grown in a liquid environment, for example where the organism is an alga. In various cases the liquid is a culture medium. In various cases the culture medium is a defined medium. Other liquid medium include fresh water, salt water, waste water, and treated water. In various cases, nutrients and other substances can be added to the liquid medium. In various cases antibiotics are added to the water.

As disclosed herein, accumulation of bioenergy carriers was assessed in two starchless mutants of *Chlamydomonas reinhardtii*, sta6 (ADP-glucose pyrophosphoryase small subunit) and sta7 (isoamylase), a control strain (CC124), and two complemented strains of sta7.

In some cases, genetic blockage of starch synthesis in sta6 and sta7 increases the accumulation of lipids on a cellular basis during nitrogen deprivation relative to the CC124 control. In some cases, lipid accumulation can be between 2- and 4-fold greater, respectively, compared to wild-type cells. In some cases, lipid accumulation can be determined by conversion to fatty acid methyl esters. In most cases, however, increased lipid accumulation can not be energetically offset by the loss of cellular starch that is synthesized by CC124 during nitrogen deprivation. In some cases, acetate utilization and $O_2$ evolution can be assayed to obtain further insights into the physiological adjustments utilized by the two starchless mutants in the absence of starch synthesis.

In some cases, sta6 and sta7 metabolize less acetate and have more severely attenuated levels of photosynthetic $O_2$ evolution relative to CC124. In some cases, these decreases can indicate an overall decrease in anabolic processes is a physiological response to nitrogen deprivation in sta6 and sta7.

Lipid and starch metabolism was also investigated in two independent sta7:STA7 complements. In various embodiments, sta7 complemented strains can accumulate more cellular starch and lipid relative to CC124 during acclimation to nitrogen deprivation. In some embodiments, complemented sta7 strains can synthesize significant quantities of starch even when cultured in nutrient-replete medium.

In many embodiments, sta6 and sta7 can accumulate more lipid relative to the CC124 control during nitrogen deprivation. In some cases, nitrogen stress can increase lipid accumulatin in sta6.

In some embodiments, a sta7, isoamylase mutant, can increase cellular lipid accumulation relative to both a control strain and sta6. In some cases, increased lipid accumumaltion can not compensate for loss of starch synthesis, from an energetic perspective. In some cases, starchless mutants have diminished $O_2$ evolution and acetate utilization during nitrogen stress.

In some embodiments, complementation of starch mutants with a wild-type starch gene can result in increased size as well as increased lipid and starch accumulation. For example, complementation of sta7 with genomic DNA encoding the wild-type isoamylase can result in cells that were larger than sta6, sta7, and CC124, accumulate high levels of lipid during nitrogen deprivation, and accumulate high levels of starch even in nutrient-replete medium.

In some embodiments, sta6 and sta7 can impede starch synthesis at different points on the biosynthetic pathway.

In various embodiments, acclimation mechanisms resulting from starchless mutants, can include several metabolic outcomes, for example partitioning of carbon precursors normally used for starch synthesis to lipid biosynthetic pathways, attenuation of cellular anabolic processes (e.g. photosynthesis, utilization of available nutrients, and carbon storage product synthesis and accumulation), and secretion of soluble sugars. In some cases, starchless mutants can not secrete soluble sugars, or evidence of secretion can not be detected. In the case of sta6 and sta7 mutants, both partitioning and attenuation were observed during nitrogen deprivation. In some cases, the greatest level of starch and lipid accumulation can occur during nitrogen deprivation.

In many cases, starchless mutants can show increased lipid accumulation on a cellular basis, for example sta6 and sta7 have increased lipid accumulation relative to CC124 during nitrogen deprivation. In some cases, lipid-derived FAMEs can be approximately 2 and 4 fold greater in sta6 and sta7, respectively, relative to CC124. In some cases, this increase can be lower when measured as a function of culture volume (~1.5 to 2 fold, respectively), because CC124 cells can continue to undergo limited cell division during the first 24 h of acclimation to nitrogen stress.

In some cases, starchless mutants can also acclimate to nitrogen stress through a decrease in overall anabolic processes. In some cases, decreases in anabolic process can bereflected by decreased levels of photosynthetic $O_2$ evolution and acetate utilization relative to CC124. For example, sta6 and sta7 can use less acetate, relative to CC124, and exhibit decreased levels of $O_2$-evolution activity. In some cases, sta6 had lower acetate uptake and $O_2$ evolution relative to CC124, even when standardized to chlorophyll.

In some embodiments, $F_v/F_m$ parameters can be higher for the starchless mutants after several days of nitrogen deprivation. In some cases, pigmentation can be lost faster in the starchless mutants relative to CC124 on agar plates. In some cases, initial lowering of $F_v/F_m$ under nitrogen deplete conditions can be a consequence of increases of $F_o$, the baseline level fluorescence prior to PSII charge separation. In many embodiments, $F_o$ can first increase, which may be due to the dissociation of PSII antenna complexes from the reaction center. Subsequent decreases can occur as the cells lose pigmentation under nitrogen-depleted conditions. For example, this can be seen in CC124, while sta6 and sta7 show a more gradual decline in $F_o$.

In some embodiments, sta7, under certain conditions, can accumulate greater amounts of cellular lipid than sta6. Increased levels of lipid accumulation have also been observed in a starchless mutant of the alga *Chlorella pyrenoidosa*. In some cases, light intensities during acclimation to nitrogen deprivation can affect reports a 10-fold increase in triacylglycerol (TAG) content relative to the control strain, CC1690. In some case, light intensity may be about 50 $\mu$moles $m^{-2}$ $s^{-1}$PAR constant illumination, or greater, for example about 2× greater, about 3× greater, about 4× greater, about 5× greater, or greater than 5×.

In some cases, increased lipid accumulation may be reflected in increased percentage of TAG, rather than an increase in total lipid. In some cases, increased TAG percentage can be measured as a function of dry weight, and increases in TAG percentage may result from increased TAG synthesis and/or the loss of carbohydrate mass.

In various embodiments, starchless mutants can be complemented, for example by transforming mutants with wild-type copies of the mutant gene. In many embodiments, complemented starchless mutants can be complemented with genomic DNA encoding the WT STA7 gene. In some embodiments, complemented starchless mutants can have cell different morphology, starch synthesis, and lipid accumulation relative to CC124 and sta7.

In some embodiments, complemented starchless mutants can accumulate levels of cellular starch in nutrient-replete medium that approach or equal cellular starch levels achieved in nitrogen-deprived CC124 cells.

In some embodiments, complemented starchless mutants can be larger than non-complemented and wild-type cells. In some embodiments complemented cells can divide, or double more slowly than non-complemented or wild-type cells. In some embodiments, complemented cells can accumulate more lipid on a cellular basis than the other cells.

In some cases, complementation may cause disregulation of starch biosynthetic genes, for example isoamylase disregulation can result from the enzyme, which is typically part of a larger protein complex, being outside its proper complex/ context, and/or enzyme levels have been perturbed resulting in increased starch synthesis.

In some cases, during nitrogen stress, complemented starchless mutants may accumulate more starch than wild-type cells. In some cases, complemented starchless mutants may accumulate about 2-fold, 3-fold, 4-fold, 5-fold, 6-fold, 7-fold, 8-fold, 9-fold, 10-fold, or more starch than wild-type cells. For example, complemented sta7 mutants can accumulate approximately 2-fold more starch than CC124 on a cellular basis. In some cases, for example during nitrogen-deprivation, during which complemented starchless mutants may divide very slowly, the increased starch content can be less pronounced on a culture volume basis relative to wild type cells.

In many embodiments, complemented starchless mutant strains can also accumulation greater quantities of lipid, on both a cellular basis and a culture-volume basis, than non-complemented and wild-type strains. In some cases, lipid accumulation can result from larger cells having larger volume for accumulation and/or more membrane that can be converted into FAMEs. In many cases, increased lipid and starch accumulation in complemented starchless strains may coincide with increased acetate utilization and oxygenic photosynthesis.

In many cases, complemented starchless mutant cells do not exhibit wild-type phenotype. In some cases, an increase in the synthesis of a primary bioenergy carrier can occur can occur because constituents used for cell division, for example proteins and nucleic acids, are not synthesized. In various embodiments, increases in starch content in complemented starchless mutant strains, during nutrient-replete culturing, can occur with decreased growth rates and increased cell size.

In some embodiments, complemented starchless strains can enter stationary phase earlier than the other strains. In some embodiments, complemented starchless mutants may accumulate starch primarily between 28 and 96 h of culturing in nutrient-replete medium. In some cases, nutrients may be limited between 28 and 96 h, resulting in a stress response.

Figure 4:
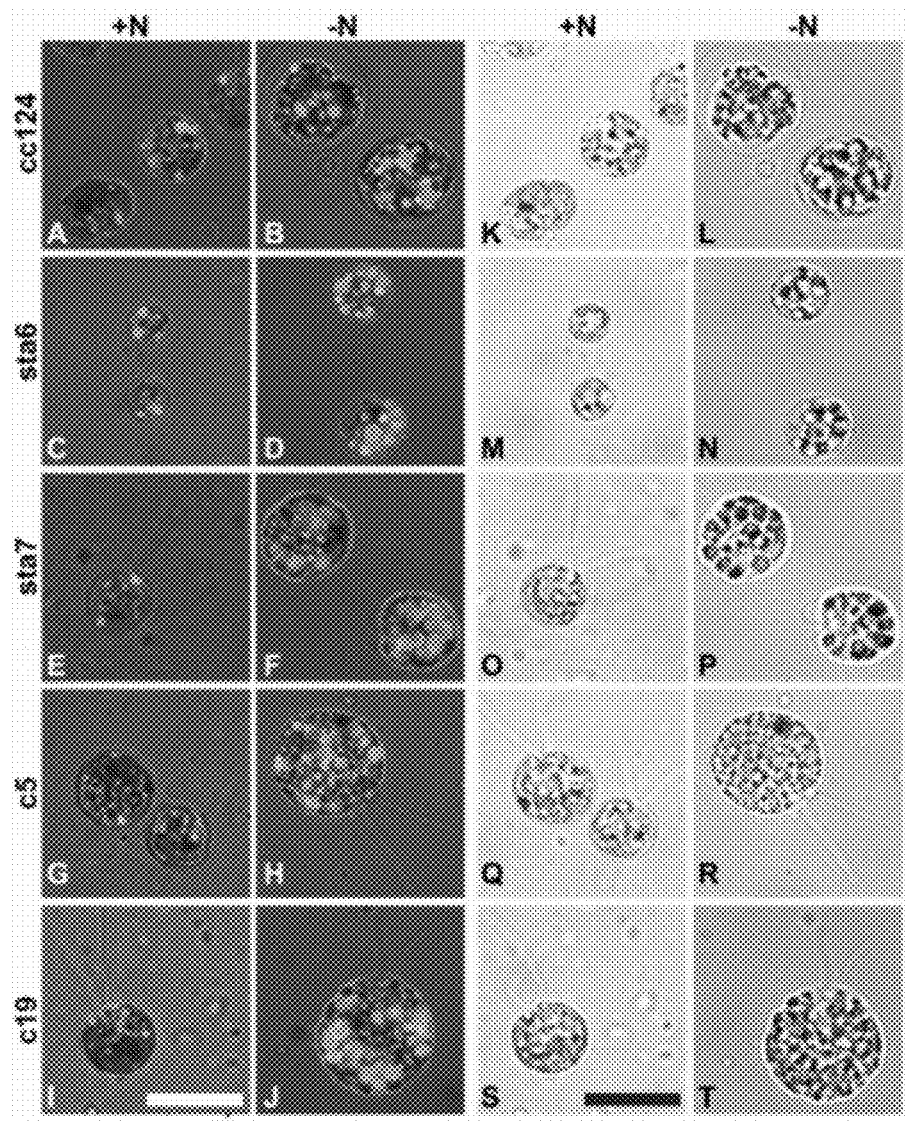
FIG. 4. Laser scanning confocal fluorescent microscopy images merged with transmitted light images. CC124, sta6, sta7, c5, and c19 cells are shown, top to bottom, respectively. The two leftmost columns show cells stained with the non-polar lipid fluorophore Bodipy 493/503. Non-polar lipid bodies are visualized by green Bodipy fluorescence after 96 h (left: TAP, right: TAP-N). The two rightmost columns show differential interference contrast images after 96 h (left: TAP, right: TAP-N). Oil bodies are visible inside the cells as blue-green tinted vesicles. Chlorophyll autofluorescence is red. All scale bars represent 10 µm.

In some embodiments, typical stress response can not involve accumulation of lipid bodies, for example, lipid body accumulation can not be observed at the end of 96 h in the complemented sta7 strains cultured in TAP (FIG. 4).

EXAMPLES

The following non-limiting examples illustrate aspects of the disclosure. Examples are provided below to illustrate the present compounds, surfaces, and methods of using the same.

sta6 (330) and sta7 (CC425) are auxotrophic for arginine, which could be used as a cellular nitrogen/carbon source. The growth curves and cell diameter data shown in FIG. 1 and Table I, respectively, show several distinguishing features. In nitrogen-replete medium, significantly different final cell densities are achieved with sta6>CC124>sta7>c5>c19. Although the highest cell concentrations measure here were attained in sta6, this strain has the smallest average cell diameter (5.6 µm). In contrast, the c5 (6.3 µm) and c19 (6.9 µm) complemented strains showed the largest average cell diameter but achieved the lowest cell densities. Intermediate cell diameters and final cell counts were observed for CC124 (5.9 µm) and sta7 (6.0 µm). The average cell diameters for each strain remained relatively stable for the entire 96 h culturing period in nitrogen-replete medium, with the exception of the c5 and c19 strains, which entered stationary phase prior to the other strains and became noticeably larger at the end of the 96 h culturing period (Table I). Additionally, results in TAP medium indicated that decreased rates of cell division are correlated with larger average cell diameters.

TABLE I

Average cell sizes for CC124, sta6, sta7, c5, and c19 cultured in TAP or TAP-N media.[a]

| | | 0 hr | | | 96 hr | | |
|---|---|---|---|---|---|---|---|
| | | Cell Diameter (µm) | Total Cellular Volume (µl/ml culture) | N | Cell Diameter (µm) | Total Cellular Volume (µl/ml culture) | N |
| N+ | CC124 | 5.93 ± 1 | 0.238 ± 0.05 | 6,524 | 5.75 ± 1.07 | 2.349 ± 0.2 | 106,695 |
| | sta6 | 5.55 ± 0.67 | 0.155 ± 0.06 | 9,390 | 5.49 ± 0.68 | 2.402 ± 0.56 | 107,748 |
| | sta7 | 6.02 ± 0.87 | 0.181 ± 0.09 | 4,657 | 6.12 ± 0.93 | 1.667 ± 0.1 | 42,933 |
| | c5 | 6.23 ± 0.93 | 0.209 ± 0.04 | 6,352 | 6.58 ± 0.85 | 1.908 ± 0.44 | 60,708 |
| | c19 | 6.75 ± 1.09 | 0.272 ± 0.11 | 6,226 | 6.92 ± 1.04 | 1.652 ± 0.41 | 44,173 |
| N− | CC124 | 5.22 ± 0.73 | 0.213 ± 0.05 | 9,172 | 7.25 ± 1.18 | 0.755 ± 0.16 | 17,157 |
| | sta6 | 4.91 ± 0.74 | 0.114 ± 0.04 | 5,451 | 5.97 ± 0.8 | 0.413 ± 0.16 | 43,649 |
| | sta7 | 5.65 ± 0.88 | 0.147 ± 0.09 | 4,374 | 6.49 ± 0.82 | 0.457 ± 0.19 | 40,533 |
| | c5 | 6.29 ± 0.92 | 0.179 ± 0.1 | 3,906 | 7.52 ± 0.99 | 0.403 ± 0.2 | 10,019 |
| | c19 | 6.36 ± 1.07 | 0.156 ± 0.08 | 3,296 | 7.45 ± 1.08 | 0.328 ± 0.2 | 7,953 |

[a]N cells were assessed with a Z2 ™ Coulter Counter ® Cell and Particle Counter at resuspension (0 h) and after 96 h in TAP and TAP-N media. Cell diameter data is reported as the mean value ± the standard deviation of the normal distribution of cell diameters, which is representative of the distribution of cell sizes in each culture. Cell diameter data represents a minimum of at least four independent biological replicates.

These examples are not meant to constrain the present invention to any particular application, mechanism, mode, or theory of operation.

Example 1

Distinct Growth Rates and Cell Sizes in the Starchless Mutants and Complemented Strains To examine the unique physiological acclimation mechanisms used in the absence of starch synthesis, the control strain (CC124), the starchless mutants (sta6 and sta7), and two sta7 complemented strains (sta7:STA7), c5 and c19, were pre-cultured to late-log phase in TAP medium. Cultures were then centrifuged and resuspended in either TAP or TAP-N medium at standardized cell numbers (~2.0–2.5×10$^6$ cells/ml). CC124 was used as a control since the parental strains of Strains and Culturing Conditions.

CC124 was obtained from the *Chlamydomonas* Center, sta6 (BAFJ5), sta7-10 (sta7 hereafter) in the CC425 background were previously isolated. The c5 and c19 complemented strains were isolated by transformation of the sta7-10 mutant with a genomic DNA segment (BamHI/KpnI fragment) encoding the WT STA7 gene, cloned into pSP124S.

Cultures were grown to late-log phase in nitrogen-replete Tris-Acetate-Phosphate (TAP) liquid medium and resuspended at 2.0–2.5×10$^6$ cells/ml in parallel in nitrogen-replete TAP or nitrogen-depleted TAP (TAP-N) media, in which NH$_4$Cl was omitted. Cells were grown under 50 µmoles m$^{-2}$ s$^{-1}$ PAR constant illumination on an orbital shaker. Samples for analysis were taken immediately after resuspension (0 h) and after 22, 48, 72, and 96 h. Cell counts and cell sizes were assessed using a Z2™ Coulter Counter® Cell and Particle Counter (Beckman-Coulter, Brea, Calif.). Cells were assumed to be spherical for diameter calculations, and background and cellular debris were excluded in all cellular count, volume, and diameter assessments.

In nitrogen-depleted medium, an increase in cell density was observed only for CC124 (~1.7 fold increase). None of the cell wall-less strains (sta6, sta7, c5, and c19) showed any significant change in cell number, indicating an arrest of cell division in these strains in nitrogen depleted-medium during the assay (FIG. 1B). In contrast to culturing in nutrient-replete medium, the average cell diameters increased for each strain during nitrogen stress. After 96 h of culturing in TAP-N, the largest cell diameters were observed for c5 (7.5 μm) and c19 (7.5 μm), followed by CC124 (7.3 μm), sta7 (6.5 μm) and sta6 (6.0 μm), respectively. Each strain exhibited an increase in average cell diameter during acclimation to nitrogen deprivation (Table I). This increase is suggestive of an increase in cellular carbon product accumulation. It should be noted that all cultures contained a distribution of cell sizes for both culturing conditions, the majority of which were within 1.0 μm of the average cell diameter (Table I). The differential growth rates and average cell diameters observed in each of the strains were consistent with significant cellular metabolic perturbations as a result of abolishing (or complementing) starch synthesis, and the accumulation of distinct intracellular carbon storage products.

Example 2

Excess Starch Accumulation in the sta7 Complemented Strains

Figure 2:
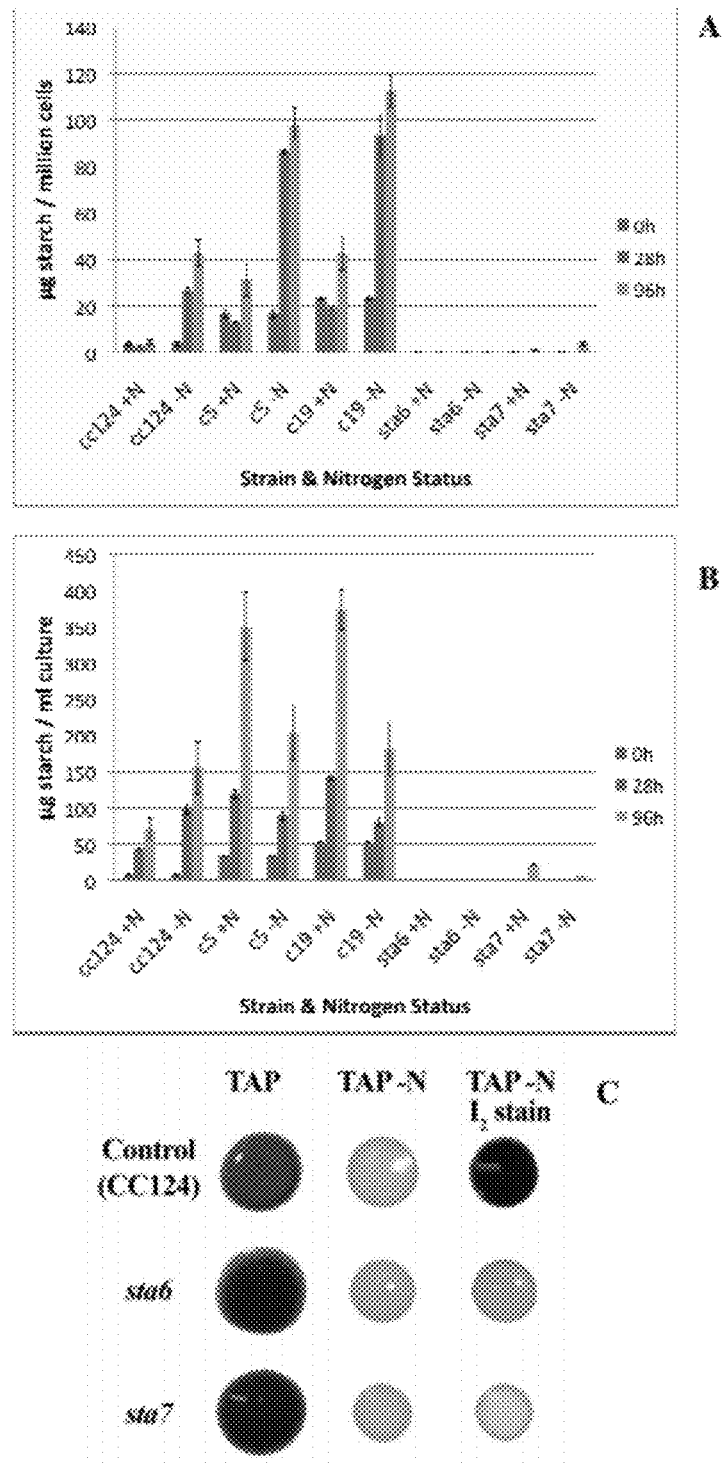
FIG. 2. Starch analyses. Cells were analyzed for glucose derived from starch after amyloglucosidase digestion at resuspension (0 h) and after 96 h in nitrogen-replete TAP or nitrogen-depleted TAP-N medium.

To assess whether the observed differences in growth rates and cell size could be correlated with the accumulation of starch and lipid, we first measured the levels of starch-derived glucose after treatment with amyloglucosidase (FIG. 2). In TAP medium, CC124 cells contained 4.5±1.0 μg starch/$10^6$ cells, measured as glucose equivalents; whereas, after four days in nitrogen-depleted medium, an approximately 10-fold cellular increase to 42.8±5.8 μg starch/$10^6$ cells was observed. Both sta6 and sta7 mutant cells contained severely attenuated levels of starch. Glucose levels were below detection in sta6, while sta7 cells contained 1.3±0.2 μg starch/$10^6$ cells in TAP and 3.8±0.7 μg starch/$10^6$ cells after four days in TAP-N medium. Remarkably, after 96 h in nutrient-replete medium, the c5 and c19 complemented strains had 31.6±7.1 μg starch/$10^6$ cells and 43.0±7.5 μg starch/$10^6$ cells, respectively—cellular levels that approach those observed in CC124 only after culturing in nitrogen-depleted medium. In fact, as shown in FIG. 2B, the highest yields of starch on a culture volume basis were attained in nitrogen-replete cultures of c5 and c9, with yields exceeding 350 mg/l after four days in cultures inoculated at 2.5×$10^6$ cells/ml. These data indicate that complementation of the sta7 mutant with a functional copy of the isoamylase enzyme significantly altered starch accumulation, and that despite transformation with a genomic copy of the STA7 gene containing native 5' and 3' UTRs and promoters, enzyme activity occurred outside of the native context resulting in modulated starch accumulation.

Starch Assays.

Cellular glucose levels contained in starch were determined using amyloglucosidase digestion and the Sigma Glucose (HK) Assay Kit (Sigma-Aldrich, St. Louis, Mo.) according to the manufacturer's instructions. Cells were concentrated by centrifugation of 10 ml culture at 3600 g for 10 min. The supernatant was discarded, and cells were frozen at −80° C. Samples were then resuspended in 100 mM sodium acetate, pH 4.5, autoclaved to solubilize starch and then digested with amyloglucosidase overnight at 60° C. to liberate glucose. To visually assess starch content in colonies on agar plates, iodine vapor staining was performed by placing solid $I_2$ pellets on the surface of agar plates to initiate sublimation.

Example 3

Increased Cellular Lipid Levels in sta6, sta7, and Complemented Strains

Figure 3:
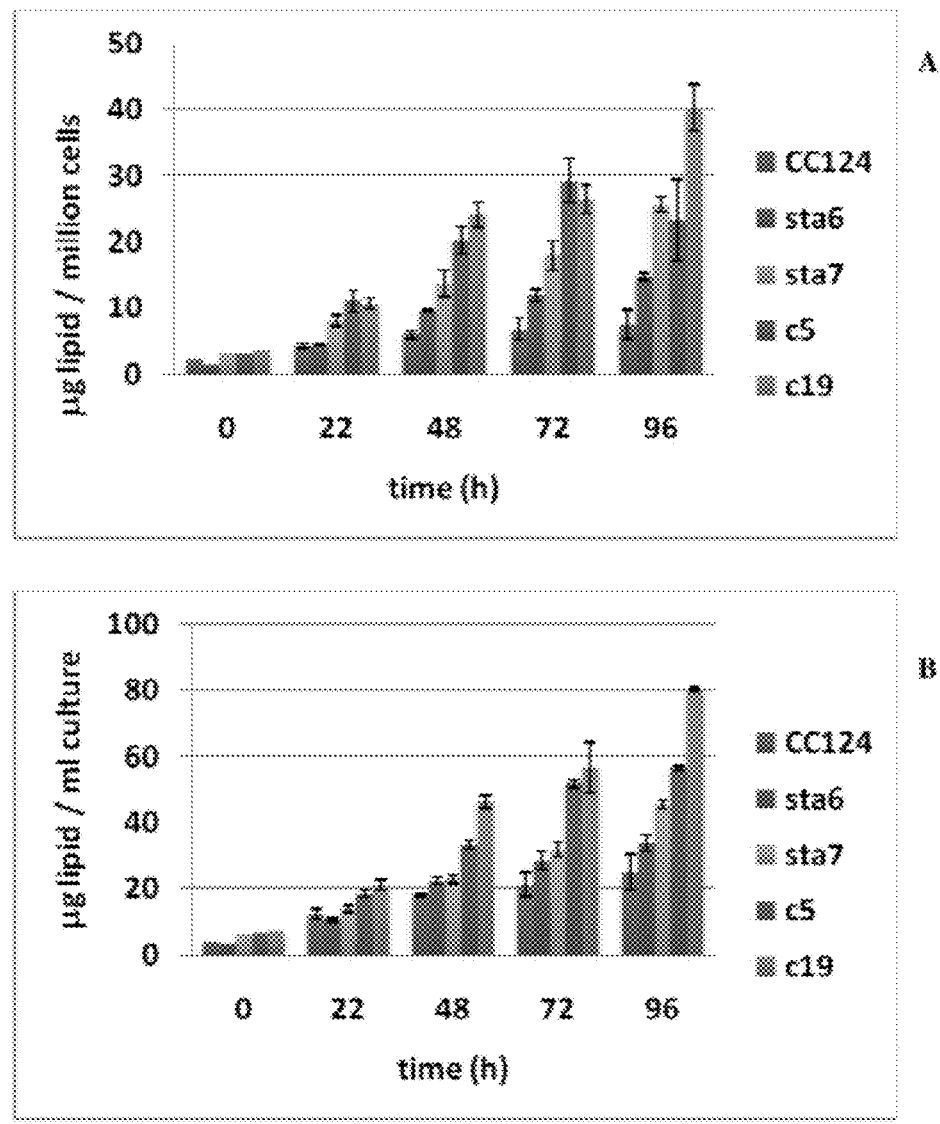
FIG. 3. GC-FID quantitation of fatty acid methyl esters derived from CC124, sta6, sta7, c5, and c19 lipids at the indicated times of culturing in nitrogen-depleted TAP-N medium. Values are representative of triplicate biological samples.

The other major carbon resource observed during nitrogen stress in C. reinhardtii is the formation of lipid bodies. Since the blockage of starch synthesis in the starchless mutants creates the potential for diverting metabolic precursors into lipid biosynthetic pathways, we investigated whether lipids were differentially accumulated in the starchless mutants by quantifying lipid-derived fatty acid methyl esters (FAMEs) using GC-FID. Lipids were extracted, derivatized, and quantified from liquid cultures of CC124, sta6, sta7, c5, and c19 at the indicated times of acclimation to nitrogen deprivation (FIG. 3). The results indicated that the greatest levels of FAMEs derived from cellular lipid are observed in c5, c19, and sta7, followed by sta6 and CC124, respectively. The starchless mutants contained approximately 2 to 4 fold more lipid/cell than CC124, indicating that additional lipid accumulated in these strains relative to CC124. This is consistent with previous studies of sta6. However, from a bioenergetic perspective, it should be noted that in TAP-N CC124, cell numbers continued to increase while the starchless mutant cell numbers did not, and that despite the increased energy density of lipids relative to starch, the increased lipid content in the starchless mutants (approximately 10-20 μg/ml of culture) does not completely offset the loss of starch (150 μg starch/ml of culture at 96 h synthesized by CC124 cultures during nitrogen deprivation). It should also be noted that our cultures were inoculated at low cell densities to compare nutrient-replete and nutrient-stressed conditions, and that by standardizing to cell counts the smaller sta6 cells are slightly underrepresented from an initial biomass perspective in these experiments.

The major fatty acids observed in all strains cultured in either TAP or TAP-N media were 16:0, 16:1, 18:0, 18:1, 18:2 and 18:3, which is consistent with previous studies. Only minor differences were observed in the fatty acid profiles among the different strains under the culturing conditions used.

FAME Quantification.

Glycerolipids were converted to fatty acids for GC-FID analysis as described previously. Lipids were extracted and derivatized from liquid culture at the indicated times. Briefly, 1.0 ml methanol saturated with NaOH was added to 0.5 ml culture and heated in tightly sealed vials at 100° C. for 2 hours, resulting in cell lysis and lipid saponification. Acid-catalyzed methylation was accomplished by adding 2 ml 1:1.2 6 N HCl/MeOH and incubating at 80° C. for 2 hours, followed by 60° C. overnight incubation. Fatty acid methyl esters were extracted into 1 ml 1:1 hexane/MTBE via gentle inversion. Extracts were washed with distilled water and analyzed directly by GC-FID using an Agilent 7890A gas chromatograph with a DB5-ms column (Agilent Technologies, Santa Clara, Calif.).

Example 4

Lipid Body Formation During Nitrogen Deprivation Visualized by Fluorescence Imaging Lipid droplet formation after acclimation to nitrogen deprivation was investigated. All strains were visually assayed for nonpolar lipid accumulation using laser scanning confocal microscopy after incubation with the nonpolar lipid fluorophore Bodipy 493/503. As shown in FIG. 4, nonpolar lipid body formation, depicted by green Bodipy 493/503 fluorescence, increased dramatically in nitrogen-stressed cells relative to cells in nutrient-replete medium, which is consistent with previous reports on the induction of lipid droplet formation in *C. reinhardtii* as a consequence of nitrogen limitation. Although the greatest density of lipid droplet formation was seen in stab cells, substantial accumulation of non-polar lipid bodies is observed in all strains, with the larger sta7, c5, and c19 cells accumulating greater quantities of cellular lipids (FIG. 3).

Microscopy.

The effects of nitrogen deprivation on nonpolar lipid accumulation were visually assayed using laser scanning confocal microscopy. After 96 h in TAP-N, all strains were stained with the nonpolar lipid fluorophore Bodipy 493/503 (Molecular Probes®, Invitrogen Corporation). To prepare the cells for imaging, 3 ml of each culture was centrifuged at 4000 g at RT for 5 min. The supernatant was removed and 100 µL of the supernatant was used to resuspend the cell pellet. 99 µl of the concentrated cell suspension was then stained with 1 µl of Bodipy 493/503 (1 mg/ml in 95% ethanol) for a final concentration of 10 µg/ml. Stained cells were incubated at RT for 5 min. To immobilize cells, 1% low melting temperature (LMT) agarose was heated to 65° C. for use as mounting medium and 5 µL of stained cell suspension was rapidly mixed with 5 µl of molten 1% LMT agarose. Five µl of this mixture was immediately transferred to a coverslip which was then inverted on a microscope slide and allowed to solidify. Coverslips were sealed with a clear epoxy (nail polish) to prevent evaporation of mounting medium during the imaging process.

Example 5

Figure 5:
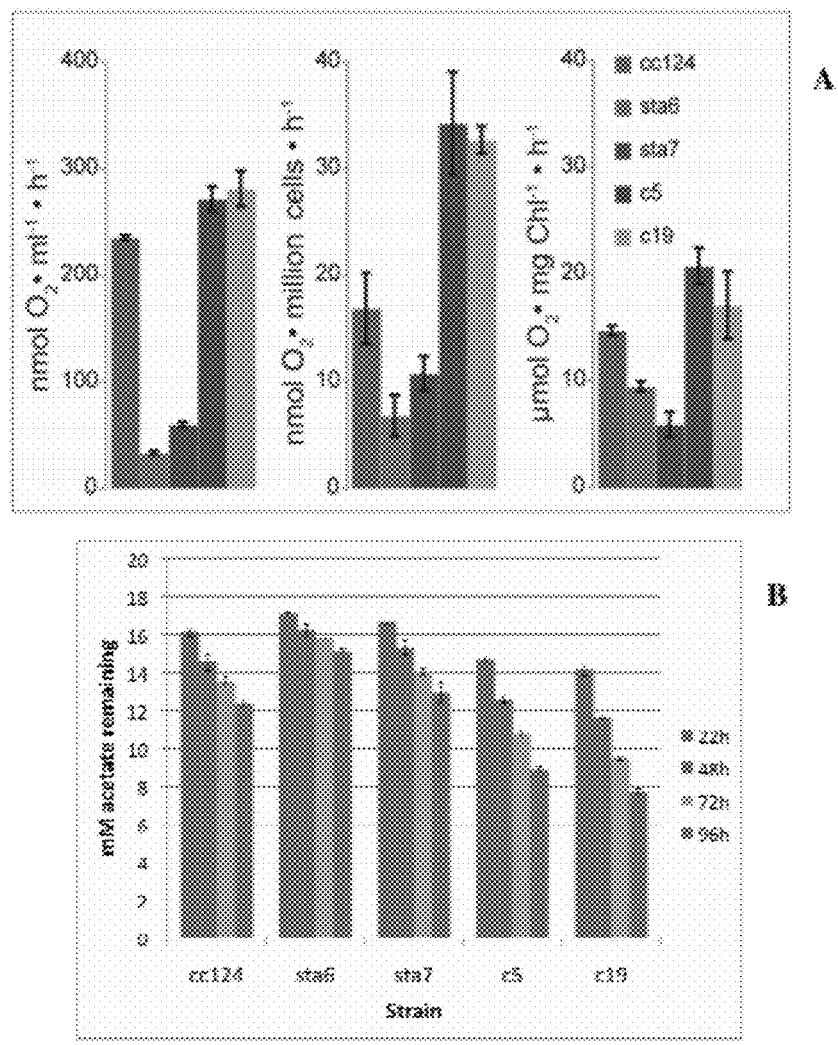
FIG. 5.

Attenuation of Photosynthetic Oxygen Evolution and Acetate Uptake in the Starchless Mutants During Nitrogen Deprivation Utilization of acetate was analyzed and the levels of photosynthetic $O_2$ evolution was quantified for each strain during acclimation to nitrogen deprivation to study mechanisms of differential carbohydrate and lipid accumulation during nitrogen deprivation and to determine whether these parameters are correlated to lipid and starch synthesis (FIG. 5). Interestingly, significant quantities of acetate remained in the medium for all strains after 96 h of nitrogen deprivation when cultures were inoculated at $2.0$–$2.5 \times 10^6$ cells/ml (FIG. 5A). More complete acetate utilization can occur if cultures were inoculated at higher cell densities. Under nutrient-replete conditions, acetate was completely consumed within 48 h (data not shown) when cells are inoculated at $2.0$–$2.5 \times 10^6$ cells/ml. These results suggested that under nutrient-replete conditions, acetate is completely consumed regardless of cellular carbohydrate and lipid levels and is presumably used to synthesize proteins, membrane lipids, and nucleic acids or support respiration during active cell division. These results indicated an overall attenuation of anabolic processes in all strains during nitrogen deprivation. However, in accordance with the starch and lipid accumulation data, acetate utilization was the greatest in c5 and c19, followed by CC124, sta7, and sta6, respectively. The increased use of acetate in the complemented c5 and c19 strains relative to the other strains, also indicated that anabolic processes in the c5 and c19 complemented strains are less severely affected during nitrogen stress.

Photosynthetic $O_2$ evolution was also monitored and all strains exhibited attenuated levels of $O_2$ evolution (20-30% of nutrient-replete levels; data not shown) after 24 h of nitrogen deprivation (FIG. 5B), relative to nutrient-replete culturing. This is consistent with previous observations that showed attenuated levels of $O_2$ evolution in *C. reinhardtii* and other algae as a consequence of a variety of nutrient (N, P, S) stresses. As shown in FIG. 5B, $O_2$ evolution in sta6 and sta7 was more severely attenuated relative to c5, c19, and CC124 during the first 24 h of nitrogen deprivation. These $O_2$ evolution data, in combination with the acetate utilization results, indicated diminished anabolic activity in the starchless mutants relative to CC124—activity that is reestablished and apparently augmented in the complemented strains. Although sta6 cultures showed the lowest levels of acetate utilization and photosynthetic activity, it should be noted again that because the average diameter of these cells is smaller relative to the other strains, and because cultures were standardized according to cell number, less cellular volume and chlorophyll was initially present in the sta6 cultures. However, even when the acetate utilization and photosynthetic activity data are adjusted to the same starting chlorophyll, oxygen evolution and acetate uptake was still attenuated in sta6 relative to CC124, c5, and c19.

Figure 6:
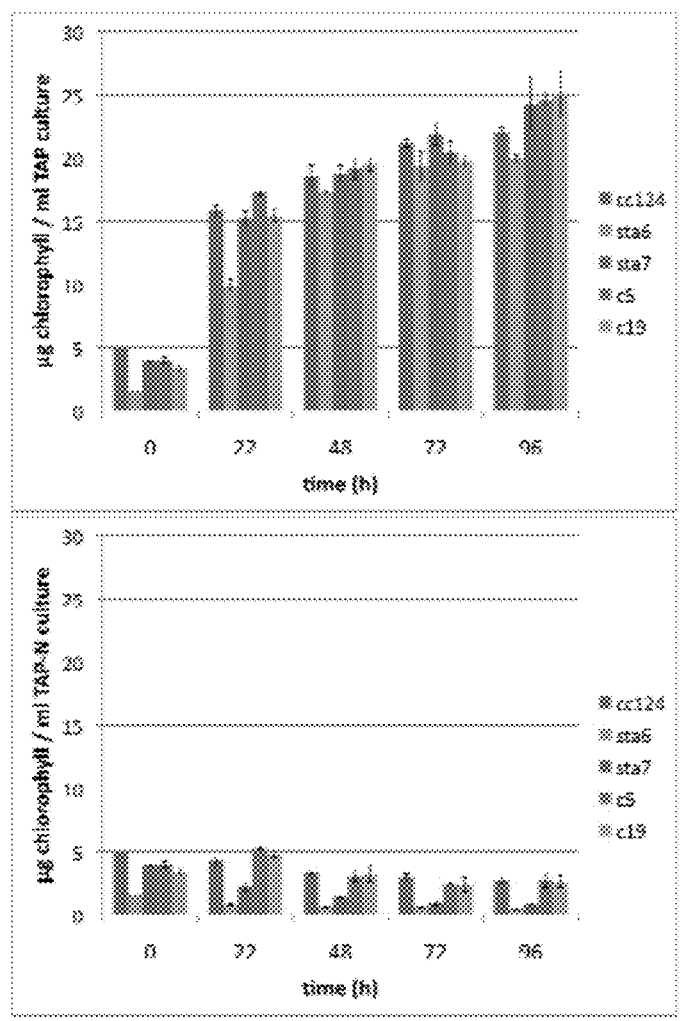
FIG. 6. Chlorophyll content per milliliter of culture in a representative experiment at specified time points for CC124, sta6, sta7, c5, and c19 in (FIG. 6A) nitrogen-replete (TAP) or (FIG. 6B) nitrogen-depleted (TAP-N) medium. Values are representative of triplicate biological samples. Cells were pre-cultured to late log phase and then resuspended at $2.0-2.5 \times 10^6$ cells/ml in either TAP or TAP-N medium.

As shown in FIG. 6, chlorophyll levels in sta6 and sta7 decreased at a greater rate in the starchless mutants than in CC124, c5, and c19 over 96 h of nitrogen deprivation. The accelerated loss of chlorophyll in the starchless mutants was consistent with the more severely attenuated $O_2$ evolution activities observed in these strains. Under nutrient-replete conditions, similar amounts of chlorophyll are attained in all strains. In sum, a significant acclimation response in the starchless mutants during nitrogen deprivation is a reduction in overall biosynthetic activity. This was reflected by diminished photosynthetic $O_2$ evolution, attenuated acetate utilization, and the observation that the mutants' increased lipid biosynthesis does not completely offset the loss of cellular starch that is synthesized by control cultures.

Acetate Utilization

Acetate remaining in culture media was quantified using HPLC as described previously (5). Both nitrogen-replete and nitrogen-depleted TAP contained 17.5 mM acetate prior to culturing (0 h). One ml of medium supernatant was filtered through a 0.45 µm Nylon membrane prior to HPLC analysis and injected into an Agilent 1200 HPLC (Agilent Technologies, Santa Clara, Calif.) equipped with an Aminex HPX-87H (Bio-Rad, Hercules, Calif.) column (45° C.), using a 0.6 ml/min flow rate and 4 mM $H_2SO_4$ as an isocratic mobile phase. UV-Vis and refractive index detectors were used to separate and quantify acetate levels by comparison with standards.

Photosynthetic Oxygen Evolution Rates.

Oxygenic photosynthesis was assessed by measuring in vivo $O_2$ production using a custom-built Clark-type apparatus equipped with YSI5331 platinum electrodes (YSI Incorporated, Yellow Springs, Ohio). Cells were grown to late-log phase under nitrogen-replete conditions, whereupon cultures were resuspended at approximately $1 \times 10^7$ cells/ml in TAP-N media to produce $O_2$ at levels sufficient for detection. Cell suspensions (0.8 ml) were taken immediately after removal from the orbital shaker and added to a temperature-controlled, water-jacketed glass reaction cell (Allen Scientific Glass, Boulder, Colo.) based on an earlier design by Gilson Inc. Probe polarization (0.6V) and digital signal amplification was accomplished using a custom-built digital picoampmeter circuit and acquired using a digital data acquisition card (National Instruments, Austin, Tex.) and custom software. Calibration of the electrode signal was done at the initiation of each experiment using air-saturated TAP medium and argon-purged (General Air, Denver, Colo.) reference buffer. Oxygen photoproduction of the stirred cell suspensions was measured during a 3-min illumination with approximately 80 µmol photons m$^{-2}$ s$^{-1}$ from an incandescent Fiber-Lite High Intensity Illuminator (Dolan-Jenner Industries, Lawrence, Mass.). Oxygen photoproduction rates were calculated from the change in O$_2$ concentration over the 3-min illumination phase. Normalizations were done based on culture volume, the amount of chlorophyll (µg), or the cell density of each sample.

Chlorophyll Measurements.

Chlorophyll was measured using ethanol extraction. One ml of culture was centrifuged at 6000 g for 5 min at room temperature (RT), the supernatant was saved for acetate quantification (see below), and the cell pellets resuspended in 95% ethanol and vortexed to extract pigments. Cellular debris was pelleted by centrifugation (14,000 g) for 3 min, and absorption was read at 665 nm and 649 nm using a Jenway 6505 UV/Vis spectrophotometer (Barloworld Scientific Ltd., Essex, U.K.). Total chlorophyll (µg/ml) calculations were performed as described previously.

Example 6

Chlorophyll Fluorescence is Able to Distinguish the Starchless Mutants from CC124

Figure 7:
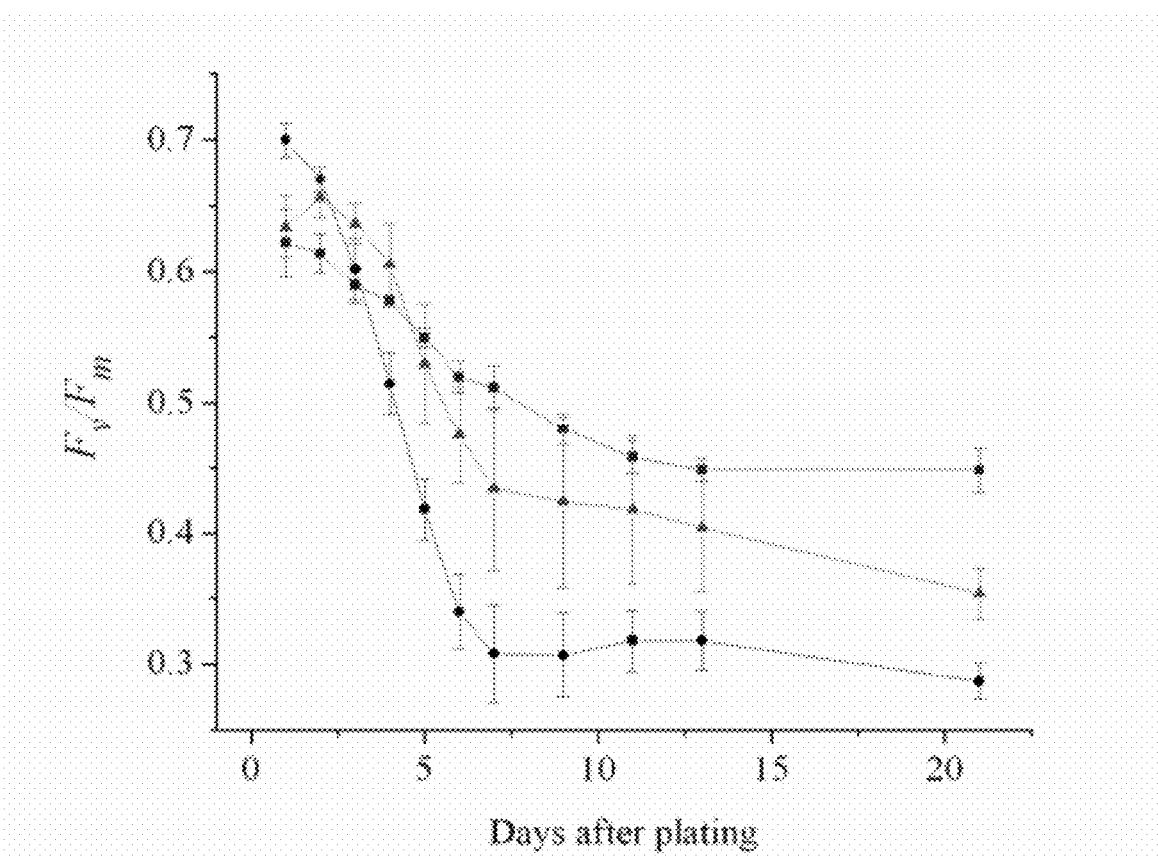
FIG. 7. Variable chlorophyll-a fluorescence ($F_v/F_m$) of CC124 (circles), sta6 (triangles), and sta7 (squares) plated on TAP-N agar (five replicate colonies for each strain) as measured by the PSI Fluor Cam imager.

To ascertain whether the starchless phenotype could be discriminated from wildtype cells using chlorophyll fluorescence techniques and adapted to downstream high-throughput screening assays for mutants that have restored anabolic and photosynthetic phenotypes, we probed the variable fluorescence ratio $F_v/F_m$ which is proportional to the quantum yield of charge separation, in sta6, sta7, and CC124. Measurements were recorded periodically after plating using the PSI Fluor Cam imager, which is amenable to high sample throughput applications. As shown in a representative long time-scale experiment in FIG. 7, when plated on TAP-N agar $F_v/F_m$ ratios are consistently higher for the starchless mutants (sta7 slightly higher than sta6), whereas $F_v/F_m$ ratios are similar on nutrient-replete TAP plates (data not shown). This indicates differential acclimation of the photosynthetic apparatus in the starchless mutants relative to the wildtype after several days of nitrogen stress.

These results indicated that the starchless mutants can have distinct fluorescent signatures that can be useful in future studies examining both perturbations in the photosynthetic electron transport chain that occur as a consequence of the blockage in starch synthesis, and identifying mutants in the starchless backgrounds that have improved photosynthetic properties.

Chlorophyll Fluorescence Measurements.

Variable chlorophyll-a fluorescence was measured using the Photon Systems Instruments (PSI) Fluor Cam 800MF (Brno, Czech Republic). CC124, sta6, and sta7 (five replicates each) were plated on TAP and TAP-N agar and measured periodically using the PSI Fluor Cam Quenching Analysis software version 6.0 edited to allow a one-minute dark pause after the measurement of $F_m$. Plates were dark adapted for 15 minutes before measurements. Saturating pulse intensity was set at 40% with actinic pulse intensity of 1000 µmol photons m$^{-2}$ s$^{-1}$. $F_o$ and $F_m$ were measured directly from each colony and reported herein as $F_v/F_m$ where $F_v=F_m-F_o$.

REFERENCES

All references disclosed herein, whether patent or non-patent, are hereby incorporated by reference as if each was included at its citation, in its entirety.

Ball, S. G. 1998. Regulation of Starch Biosynthesis, p. 549-567. In J.-D. Rochaix, M. Goldschmidt-Clermont, and S. Merchant (eds.), The Molecular Biology of Chloroplasts and Mitochondria in *Chlamydomonas*. Kluwer Academic Publishers, Dordrecht.

Ball, S. G. 2002. The intricate pathway of starch biosynthesis and degradation in the monocellular alga *Chlamydomonas reinhardtii*. Austr. J. Chem. 55:49-59.

Ball, S. G., and P. Deschamps. 2009. Starch Metabolism, p. 1-40. In D. Stern (ed.), The *Chlamydomonas* Sourcebook, Second Edition: Organellar and Metabolic Processes, vol. 2. Academic Press, Oxford.

Chochois, V., D. Dauvillee, A. Beyl), D. Tolleter, S. Cuine, H. Timpano, S. Ball, L. Cournac, and G. Peltier. 2009. Hydrogen production in *Chlamydomonas*: photosystem II-dependent and -independent pathways differ in their requirement for starch metabolism. Plant Physiol. 151:631-640.

Datar, R., J. Huang, P.-C. Maness, A. Mohagheghi, S. Czernik, and E. Chornet. 2007. Hydrogen production from the fermentation of corn stover biomass pretreated with a steam-explosion process. Int. J. Hyd. Energy 32:932-939.

Dauvillee, D., C. Colleoni, G. Mouille, A. Buleon, D. J. Gallant, B. Bouchet, M. K. Morell, C. d'Hulst, A. M. Myers, and S. G. Ball. 2001. Two loci control phytoglycogen production in the monocellular green alga *Chlamydomonas reinhardtii*. Plant Physiol. 125:1710-1722.

Dauvillee, D., C. Colleoni, G. Mouille, M. K. Morell, C. d'Hulst, F. Wattebled, L. Lienard, D. Delvalle, J. P. Ral, A. M. Myers, and S. G. Ball. 2001. Biochemical characterization of wild-type and mutant isoamylases of *Chlamydomonas reinhardtii* supports a function of the multimeric enzyme organization in amylopectin maturation. Plant Physiol. 125:1723-1731.

Dauvillee, D., C. Colleoni, E. Shaw, G. Mouille, C. D'Hulst, M. Morell, M. S. Samuel, B. Bouchet, D. J. Gallant, A. Sinskey, and S. Ball. 1999. Novel, starch-like polysaccharides are synthesized by an unbound form of granule-bound starch synthase in glycogen-accumulating mutants of *Chlamydomonas reinhardtii*. Plant Physiol. 119:321-330.

Dauvillee, D., V. V. Mestre, C. Colleoni, M. Slomianny, G. Mouille, B. Delrue, C. d'Hulst, C. Bliard, J. Nuzillard, and S. Ball. 2000. The debranching enzyme complex missing in glycogen accumulating mutants of *Chlamydomonas reinhardtii* displays an isoamylase-type specificity. Plant Sci. 157:145-156.

Dismukes, G. C., D. Carrieri, N. Bennette, G. M. Ananyev, and M. C. Posewitz. 2008. Aquatic phototrophs: efficient alternatives to land-based crops for biofuels. Curr. Opin. Biotechnol. 19:235-240.

Ghirardi, M. L., M. C. Posewitz, P. C. Maness, A. Dubini, J. Yu, and M. Seibert. 2007. Hydrogenases and hydrogen photoproduction in oxygenic photosynthetic organisms. Annu. Rev. Plant Biol. 58:71-91.

Gocze, P. M., and D. A. Freeman. 1994. Factors Underlying the Variability of Lipid Droplet Fluorescence in Ma-10 Leydig Tumor-Cells. Cytometry 17:151-158.

Gorman, D. S., and R. P. Levine. 1965. Cytochrome f and plastocyanin: their sequence in the photosynthetic electron transport chain of *Chlamydomonas reinhardi*. Proc. Nat. Acad. Sci. U.S.A. 54:1665-1669.

Grossman, A. R., M. Croft, V. N. Gladyshev, S. S. Merchant, M. C. Posewitz, S. Prochnik, and M. H. Spalding. 2007. Novel metabolism in *Chlamydomonas* through the lens of genomics. Curr. Opin. Plant Biol. 10:190-198.

Hankamer, B., F. Lehr, J. Rupprecht, J. H. Mussgnug, C. Posten, and O. Kruse. 2007. Photosynthetic biomass and H2 production by green algae: from bioengineering to bioreactor scale-up. Physiol. Plant 131:10-21.

Harris, E. E. 2009. *Chlamydomonas* in the laboratory, p. 241-262. In E. Harris (ed.), The *Chlamydomonas* Sourcebook, Second Edition: Organellar and Metabolic Processes, vol. 1. Academic Press, Oxford.

Harris, E. H. 1989. The *Chlamydomonas* Sourcebook, p. 1-780. In E. Harris (ed.), The *Chlamydomonas* Sourcebook: a comprehensive guide to biology and laboratory use. Academic Press, San Diego.

Hemschemeier, A., A. Melis, and T. Happe. 2009. Analytical approaches to photobiological hydrogen production in unicellular green algae. Photosynth Res.

Herzig, R., and P. G. Falkowski. 1989. Nitrogen Limitation in *Isochrysis-Galbana* (Haptophyceae).1. Photosynthetic Energy-Conversion and Growth Efficiencies. J. Phycology 25:462-471.

Hu, Q., M. Sommerfeld, E. Jarvis, M. Ghirardi, M. Posewitz, M. Seibert, and A. Darzins. 2008. Microalgal triacylglycerols as feedstocks for biofuel production: perspectives and advances. Plant J. 54:621-639.

Karns, D. 2009. M. S. thesis, Colorado School of Mines, Golden.

Kolber, Z. S., O. Prasil, and P. G. Falkowski. 1998. Measurements of variable chlorophyll fluorescence using fast repetition rate techniques: defining methodology and experimental protocols. Biochim. Biophys. Acta 1367:88-106.

Kruse, O., J. Rupprecht, J. H. Mussgnug, G. C. Dismukes, and B. Hankamer. 2005. Photosynthesis: a blueprint for solar energy capture and biohydrogen production technologies. Photochem. Photobiol. Sci. 4:957-970.

Li, Y., D. Han, G. Hu, D. Dauvillee, M. Sommerfeld, S. Ball, and Q. Hu. 2010. *Chlamydomonas* starchless mutant defective in ADP-glucose pyrophosphorylase hyper-accumulates triacylglycerol. Metab. Eng.

Libessart, N., M. L. Maddelein, N. Koornhuyse, A. Decq, B. Delrue, G. Mouille, C. D'Hulst, and S. Ball. 1995. Storage, Photosynthesis, and Growth: The Conditional Nature of Mutations Affecting Starch Synthesis and Structure in *Chlamydomonas*. Plant Cell 7:1117-1127.

Lumbreras, V., D. R. Stevens, and S. Purton. 1998. Efficient foreign gene expression in *Chlamydomonas reinhardtii* mediated by an endogenous intron. Plant J. 14:441-447.

Martin, N. C., and U. W. Goodenough. 1975. Gametic differentiation in *Chlamydomonas reinhardtii*. I. Production of gametes and their fine structure. J. Cell Biol. 67:587-605.

Melis, A., L. Zhang, M. Forestier, M. L. Ghirardi, and M. Seibert. 2000. Sustained photobiological hydrogen gas production upon reversible inactivation of oxygen evolution in the green alga *Chlamydomonas reinhardtii*. Plant Physiol. 122:127-136.

Merchant, S. S., S. E. Prochnik, O. Vallon, E. H. Harris, S. J. Karpowicz, G. B. Witman, A. Terry, A. Salamov, L. K. Fritz-Laylin, L. Marechal-Drouard, W. F. Marshall, L. H. Qu, D. R. Nelson, A. A. Sanderfoot, M. H. Spalding, V. V. Kapitonov, Q. Ren, P. Ferris, E. Lindquist, H. Shapiro, S. M. Lucas, J. Grimwood, J. Schmutz, P. Cardol, H. Cerutti, G. Chanfreau, C. L. Chen, V. Cognat, M. T. Croft, R. Dent, S. Dutcher, E. Fernandez, H. Fukuzawa, D. Gonzalez-Ballester, D. Gonzalez-Halphen, A. Hallmann, M. Hanikenne, M. Hippler, W. Inwood, K. Jabbari, M. Kalanon, R. Kuras, P. A. Lefebvre, S. D. Lemaire, A. V. Lobanov, M. Lohr, A. Manuell, I. Meier, L. Mets, M. Mittag, T. Mittelmeier, J. V. Moroney, J. Moseley, C. Napoli, A. M. Nedelcu, K. Niyogi, S. V. Novoselov, I. T. Paulsen, G. Pazour, S. Purton, J. P. Ral, D. M. Riano-Pachon, W. Riekhof, L. Rymarquis, M. Schroda, D. Stern, J. Umen, R. Willows, N. Wilson, S. L. Zimmer, J. Allmer, J. Balk, K. Bisova, C. J. Chen, M. Elias, K. Gendler, C. Hauser, M. R. Lamb, H. Ledford, J. C. Long, J. Minagawa, M. D. Page, J. Pan, W. Pootakham, S. Roje, A. Rose, E. Stahlberg, A. M. Terauchi, P. Yang, S. Ball, C. Bowler, C. L. Dieckmann, V. N. Gladyshev, P. Green, R. Jorgensen, S. Mayfield, B. Mueller-Roeber, S. Rajamani, R. T. Sayre, P. Brokstein, I. Dubchak, D. Goodstein, L. Hornick, Y. W. Huang, J. Jhaveri, Y. Luo, D. Martinez, W. C. Ngau, B. Otillar, A. Poliakov, A. Porter, L. Szajkowski, G. Werner, K. Zhou, I. V. Grigoriev, D. S. Rokhsar, and A. R. Grossman. 2007. The *Chlamydomonas* genome reveals the evolution of key animal and plant functions. Science 318:245-250.

Moellering, E. R., and C. Benning. 2009. RNAi Silencing of a major lipid droplet protein affects lipid droplet size in *Chlamydomonas reinhardtii*. Eukaryot. Cell. 31.

Mouille, G., M. L. Maddelein, N. Libessart, P. Talaga, A. Decq, B. Delrue, and S. Ball. 1996. Preamylopectin Processing: A Mandatory Step for Starch Biosynthesis in Plants. Plant Cell 8:1353-1366.

Pendergrass, S., and P. Jensen. 1997. Application of the gas chromatography-fatty acid methyl ester system for the identification of environmental and clinical isolates of the family Micrococcaceae. Appl. Occup. Environ. Hygiene 12:543-546.

Pendergrass, S. M. 1998. Aerobic Bacteria by GC-FAME Method 0801, NIOSH Manual of Analytical Methods, 4th ed.

Posewitz, M. C., A. Dubini, J. E. Meuser, M. Seibert, and M. L. Ghirardi. 2009. Hydrogenases, Hydrogen Production and Anoxia, p. 217-255. In D. Stern (ed.), The *Chlamydomonas* Sourcebook, Second Edition: Organellar and Metabolic Processes, vol. 2. Academic Press, Oxford.

Posewitz, M. C., P. W. King, S. L. Smolinski, R. D. Smith, A. R. Ginley, M. L. Ghirardi, and M. Seibert. 2005. Identification of genes required for hydrogenase activity in *Chlamydomonas reinhardtii*. Biochem. Soc. Trans. 33:102-104.

Posewitz, M. C., S. L. Smolinski, S. Kanakagiri, A. Melis, M. Seibert, and M. L.

Ghirardi. 2004. Hydrogen photoproduction is attenuated by disruption of an isoamylase gene in *Chlamydomonas reinhardtii*. Plant Cell 16:2151-2163.

Ramazanov, A., and Z. Ramazanov. 2006. Isolation and characterization of a starchless mutant of *Chlorella pyrenoidosa* STL-PI with a high growth rate, and high protein and polyunsaturated fatty acid content. Phycol. Res. 54:255-259.

Sager, R., and S. Granick. 1954. Nutritional control of sexuality in *Chlamydomonas reinhardtii*. J. Gen. Physiol. 37:729-742.

Schenk, P., S. Thomas-Hall, E. Stephens, U. Marx, J. Mussgnug, C. Posten, O. Kruse, and B. Hankamer. 2008. Second Generation Biofuels: High-Efficiency Microalgae for Biodiesel Production. Bioenerg. Res. 1:20-43.

Wang, Z. T., N. Ullrich, S. Joo, S. Waffenschmidt, and U. Goodenough. 2009. Algal lipid bodies: stress induction, purification, and biochemical characterization in wild-type and starchless *Chlamydomonas reinhardtii*. Eukaryot. Cell 8:1856-1868.

Wykoff, D. D., J. P. Davies, A. Melis, and A. R. Grossman. 1998. The regulation of photosynthetic electron transport during nutrient deprivation in *Chlamydomonas reinhardtii*. Plant Physiol. 117:129-139.

Zabawinski, C., N. Van Den Koornhuyse, C. D'Hulst, R. Schlichting, C. Giersch, B. Delrue, J. M. Lacroix, J. Preiss, and S. Ball. 2001. Starchless mutants of *Chlamydomonas reinhardtii* lack the small subunit of a heterotetrameric ADP-glucose pyrophosphorylase. J. Bacteriol. 183:1069-1077.

Although the present disclosure has been described with a certain degree of particularity, it is understood the disclosure has been made by way of example, and changes in detail or structure may be made without departing from the spirit of the disclosure as defined in the appended claims.

We claim:

1. A modified algae cell comprising:
one or more copies of an isoamylase expression construct; wherein synthesis of starch by the modified algae cell is increased relative to an unmodified algae cell, and starch accumulation by the modified algae cell is increased more than about two-fold relative to the unmodified cell, and
wherein the background lacks mutations in the starch biosynthetic pathway.

2. The modified algae cell of claim 1, wherein the expression construct comprises a copy of the genomic isoamylase gene.

3. The modified algae cell of claim 1, wherein the expression construct is integrated at one or more positions in the genome.

4. The modified algae cell of claim 1, wherein the algae is a green or red algae.

5. The modified algae cell of claim 1, wherein the expression construct comprises a genomic sequence of *Chlamydomonas reinhardtii* isoamylase.

6. The modified algae cell of claim 1, wherein isoamylase is over-expressed compared to an unmodified algae cell.

7. The modified algae cell of claim 5, wherein the isoamylase expression construct comprises an isoamylase coding sequence that codes for an isoamylase enzyme with higher activity than a *Chlamydomonas reinhardtii* isoamylase enzyme.

8. A method of producing starch from an algae cell comprising: growing a modified algae cell in a growth medium, wherein the modified algae cell comprises:
one or more copies of an isoamylase expression construct, in a background lacking mutations in the starch biosynthetic pathway;
wherein synthesis of starch by the modified algae cell is increased relative to an unmodified algae cell, and starch accumulation by the modified algae cell is increased more than about two-fold relative to the unmodified cell;
isolating the algae cell from a growth medium; and
processing the algae cell to produce a starch.

9. The method of claim 8, wherein the growth medium is a nitrogen replete medium.

10. The method of claim 8, wherein the starch is included in a biofuel.

11. The method of claim 8, wherein the algae cell is *Chlamydomonas reinhardtii*.

12. The method of claim 11, wherein the isoamylase expression construct comprises a genomic isoamylase coding sequence.

13. The method of claim 11, wherein the isoamylase expression construct comprises an isoamylase coding sequence.

14. The method of claim 11, wherein the isoamylase expression construct comprises a non-*Chlamydomonas reinhardtii* isoamylase coding sequence.

15. A modified *Chlamydomonas reinhardtii* algae comprising: one or more copies of an isoamylase expression construct comprising a *Chlamydomonas reinhardtii* genomic isoamylase coding sequence;
wherein synthesis of starch by the modified algae is increased relative to the unmodified algae, and starch accumulation by the modified algae cell is increased more than about two-fold relative to the unmodified cell, and
the background lacks mutations in the starch biosynthetic pathway.

16. The modified algae of claim 15, wherein a ml culture of the modified algae produces greater than 2-fold the amount of starch compared to a ml of culture produced by CC124.

* * * * *